United States Patent
Reed et al.

(10) Patent No.: US 11,369,672 B2
(45) Date of Patent: Jun. 28, 2022

(54) **COMPOSITIONS AND METHODS FOR TREATING AN ACTIVE *MYCOBACTERIUM TUBERCULOSIS* INFECTION**

(71) Applicant: ACCESS TO ADVANCED HEALTH INSTITUTE, Seattle, WA (US)

(72) Inventors: Steven G. Reed, Bellevue, WA (US); Rhea N. Coler, Seattle, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 0 days.

(21) Appl. No.: 16/126,285

(22) Filed: Sep. 10, 2018

(65) Prior Publication Data
US 2020/0038498 A1 Feb. 6, 2020

Related U.S. Application Data

(63) Continuation of application No. 14/419,477, filed as application No. PCT/US2013/053482 on Aug. 2, 2013, now abandoned.

(60) Provisional application No. 61/791,213, filed on Mar. 15, 2013, provisional application No. 61/679,612, filed on Aug. 3, 2012.

(51) Int. Cl.
| | | |
|---|---|---|
| *A61K 39/04* | (2006.01) | |
| *A61K 31/4409* | (2006.01) | |
| *A61K 31/496* | (2006.01) | |
| *A61K 39/39* | (2006.01) | |
| *A61K 45/06* | (2006.01) | |
| *A61K 39/00* | (2006.01) | |

(52) U.S. Cl.
CPC .......... *A61K 39/04* (2013.01); *A61K 31/4409* (2013.01); *A61K 31/496* (2013.01); *A61K 39/39* (2013.01); *A61K 45/06* (2013.01); *A61K 2039/545* (2013.01); *A61K 2039/55511* (2013.01); *A61K 2039/70* (2013.01)

(58) Field of Classification Search
None
See application file for complete search history.

(56) References Cited

U.S. PATENT DOCUMENTS

| | | | | |
|---|---|---|---|---|
| 2008/0131466 A1* | 6/2008 | Reed | ...................... | A61K 45/06 424/282.1 |
| 2010/0129391 A1* | 5/2010 | Reed | ...................... | A61K 39/04 424/190.1 |

FOREIGN PATENT DOCUMENTS

WO WO-2010010178 A1 * 1/2010 ............. A61K 39/04

OTHER PUBLICATIONS

See Harrisons Principles of Internal Medicine 16th Edition, 2005, p. 953-966.*
PR Newswire. Aeras and IDRI Sign Agreement to Jointly Develop Novel Tuberculosis Vaccine. Sep. 5, 2012.*
Application No. MX/a/2015/001557, First Office Action, dated Aug. 28, 2019, 8 pages.
Application No. MX/a/2015/001557, Second Office Action, dated Jul. 31, 2020, 10 pages.
Application No. MX/a/2015/001557, Third Office Action, dated Dec. 8, 2020, 7 pages.
BR 11 2015 002483-1—Written Opinion, dated Dec. 7, 2021, 12 pages, (with English translation).
BR 11 2015 002483-1—Rejection Decision, dated May 3, 2022, 16 pages, (with English translation).

* cited by examiner

*Primary Examiner* — Oluwatosin A Ogunbiyi
(74) *Attorney, Agent, or Firm* — Newport IP, LLC; Benjamin A. Keim

(57) ABSTRACT

The present disclosure relates to methods and compositions for treating a active tuberculosis infection and methods and compositions for improving the efficacy of chemotherapy regimens against active tuberculosis infection. The present disclosure relates to methods of treating an active *M. tuberculosis* infection or an active infection resulting from reactivation of a latent infection in a mammal and to methods of improving the efficacy of chemotherapy regimens against active *M. tuberculosis* infection.

25 Claims, 13 Drawing Sheets

Specification includes a Sequence Listing.

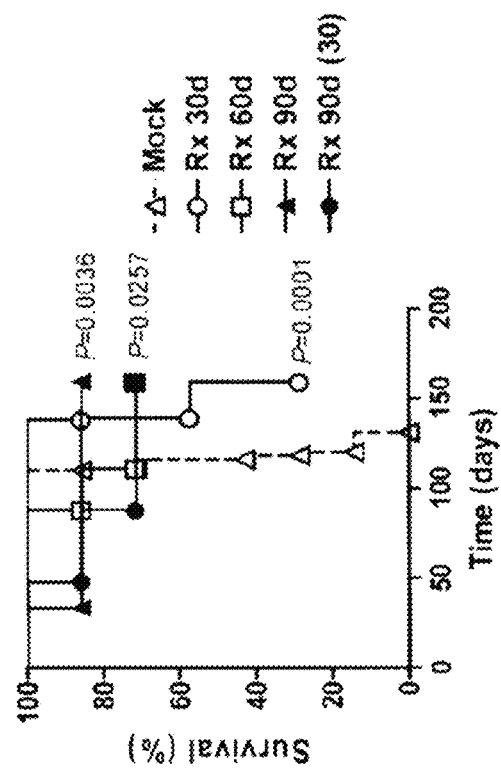
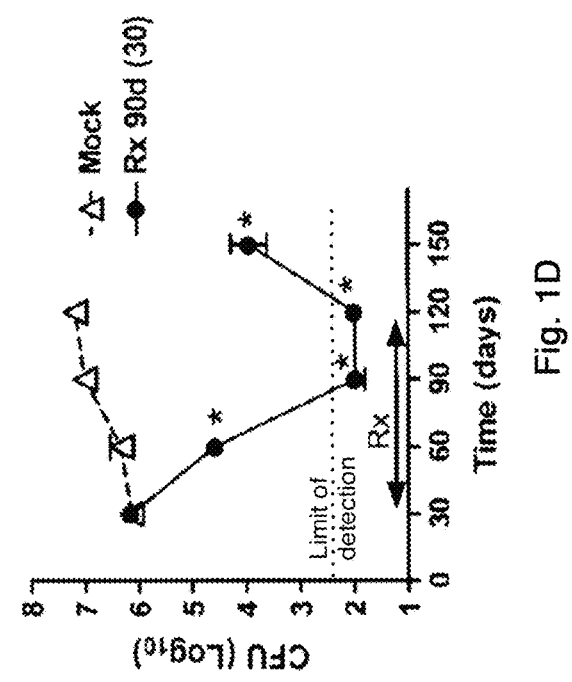
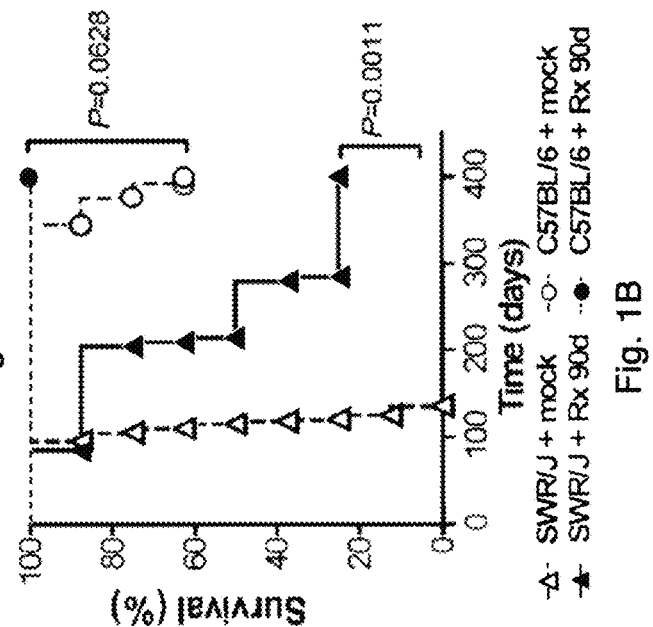

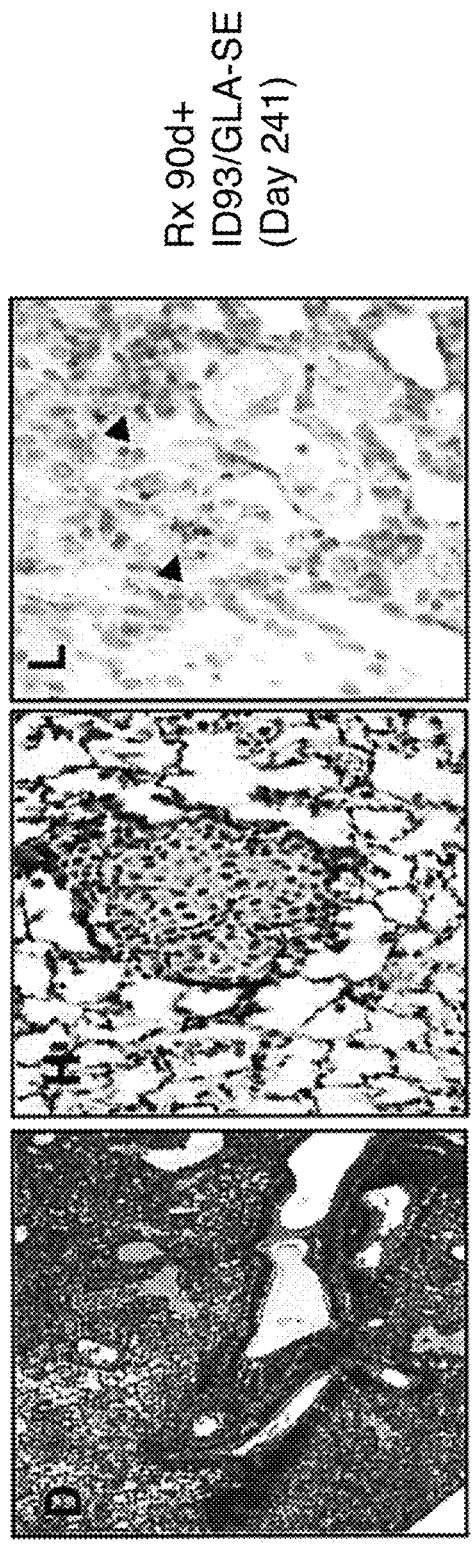
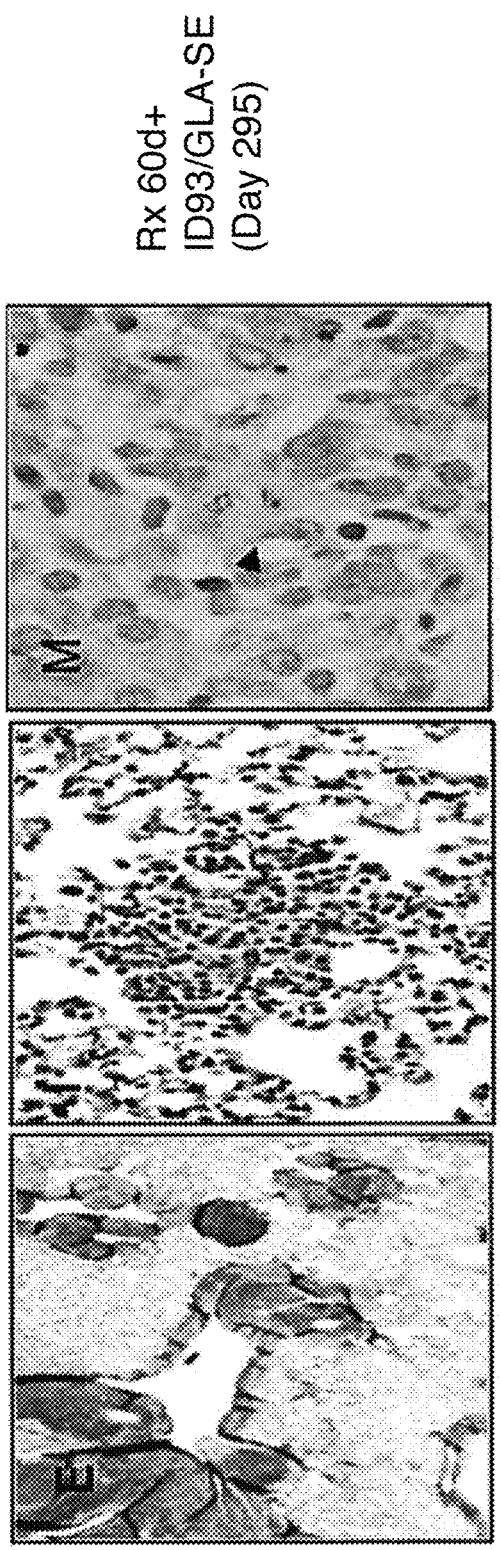

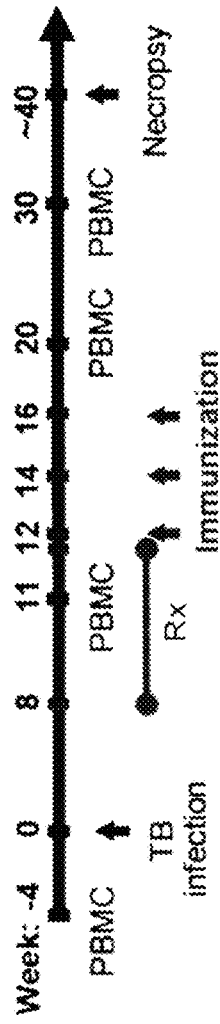
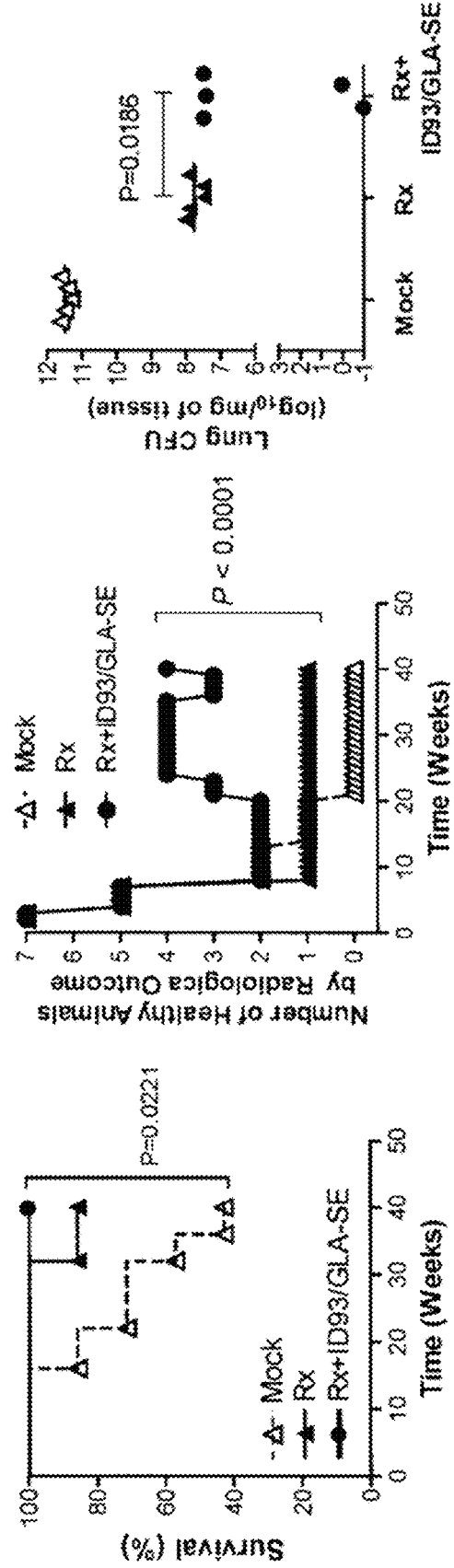
Fig. 5A
Fig. 5B
Fig. 5C
Fig 5D

Fig. 5E

COMPOSITIONS AND METHODS FOR TREATING AN ACTIVE *MYCOBACTERIUM TUBERCULOSIS* INFECTION

CROSS-REFERENCE TO RELATED PATENT APPLICATIONS

This application is a continuation of U.S. patent application Ser. No. 14/419,477, which is a national stage entry pursuant to 35 U.S.C. § 371 of International Application No. PCT/US2013/053482, filed Aug. 2, 2013, which claims the priority benefit of U.S. provisional application Ser. No. 61/679,612, filed Aug. 3, 2012, and 61/791,213, filed Mar. 15, 2013, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 712192000940SeqList.txt, date recorded: Jul. 31, 2013 size: 36 KB).

BACKGROUND

Technical Field

The present disclosure relates to methods and compositions for treating a primary active *M. tuberculosis* infection or an active infection resulting from reactivation of a latent infection in a mammal and to methods and compositions for improving the efficacy of chemotherapy regimens against active *M. tuberculosis* infection.

Description of the Related Art

Tuberculosis (TB) is a chronic infectious disease caused by infection with *Mycobacterium tuberculosis* and other *Mycobacterium* species. TB is a major pandemic disease in developing countries, as well as an increasing problem in developed areas of the world, claiming between 1.7 and 2 million lives annually. Although infection may be asymptomatic for a considerable period of time, the disease is most commonly manifested as an acute inflammation of the lungs, resulting in fever and a nonproductive cough. If untreated, serious complications and death typically result. The increase of multidrugresistant TB (MDR-TB) further heightens this threat (Dye, *Nat Rev Microbiol* 2009; 7:81-7).

The course of a *M. tuberculosis* infection runs essentially through 3 phases. During the acute or active phase, the bacteria proliferate or actively multiply at an exponential, logarithmic, or semilogrithmic rate in the organs, until the immune response increases to the point at which it can control the infection whereupon the bacterial load peaks and starts declining. Although the mechanism is not fully understood it is believed that sensitized CD4+ T lymphocytes in concert with interferon gamma (IFN-gamma, γ-IFN) mediate control of the infection. Once the active immune response reduces the bacterial load and maintains it in check at a stable and low level, a latent phase is established. Previously, studies reported that during latency *M. tuberculosis* goes from active multiplication to dormancy, essentially becoming non-replicating and remaining inside the granuloma. However, recent studies have demonstrated that even in latency, the stage of infection characterized by constant low bacterial numbers, at least part of the bacterial population remain in a state of active metabolism. (Talaat et al. 2007, *J of Bact* 189, 4265-74).

These bacteria therefore survive, maintain an active metabolism and minimally replicate in the face of a strong immune response. In the infected individual during latency there is therefore a balance between non-replicating bacteria (that may be very difficult for the immune system to detect as they are located intracellularly) and slowly replicating bacteria. In some cases, the latent infection enters reactivation, where the dormant bacteria start replicating again albeit at rates somewhat lower than the initial infection. It has been suggested that the transition of *M. tuberculosis* from primary infection to latency is accompanied by changes in gene expression (Honer zu Bentrup, 2001). It is also likely that changes in the antigen-specificity of the immune response occur, as the bacterium modulates gene expression during its transition from active replication to dormancy. The full nature of the immune response that controls latent infection and the factors that lead to reactivation are largely unknown. However, there is some evidence for a shift in the dominant cell types responsible. While CD4 T cells are essential and sufficient for control of infection during the acute phase, studies suggest that CD8 T cell responses are more important in the latent phase. Bacteria in this stage are typically not targeted by most of the preventive vaccines that are currently under development in the TB field as exemplified by the lack of activity when classical preventive vaccines are given to latently infected experimental animals (Turner et al. 2000 *Infect Immun*. 68:6:3674-9).

Although TB can generally be controlled using extended antibiotic therapy, such treatment is not sufficient to prevent the spread of the disease. Infected individuals may be asymptomatic, but contagious, for some time. Current clinical practice for latent TB (asymptomatic and non-contagious) is treatment with 6 to 9 months of isoniazid or other antibiotic or alternatively 4 months of rifampin. Active TB is treated with a combination of 4 medications for 6 to 8 weeks during which the majority of bacilli are thought to be killed, followed by two drugs for a total duration of 6 to 9 months. Duration of treatment depends on the number of doses given each week. In addition, although compliance with the treatment regimen is critical, patient behavior is difficult to monitor. Some patients do not complete the course of treatment either due to side effects or the extreme duration of treatment (6-9 months), which studies have shown can lead to ineffective treatment and the development of drug resistance.

In order to control the spread of tuberculosis, both effective prophylactic vaccination and accurate early diagnosis of active disease followed by more effective therapeutic regimes including therapeutic vaccines and cost effective and patient accepted chemotherapeutics is of utmost importance. Currently prophylactic vaccination with live bacteria such as *Bacillus* Calmette-Gueerin (BCG), an avirulent strain of *M. bovis*, is the most efficient method for inducing protective immunity. However, the safety and efficacy of BCG is a source of controversy and some countries, such as the United States, do not vaccinate the general public with this agent. The development of molecular adjuvants, combined with select recombinant proteins, has enabled the development of a new generation of vaccines that may be used prophylactically as well as therapeutically to treat, as well as prevent infectious diseases. See, e.g., EP 2457926. What is needed is a therapeutic vaccine that is effective in stimulating an immune response for active TB disease even in the face of high bacterial burden in order to provide an adjunct to chemotherapeutics to reduce the treatment time, clear bacilli, limit lung pathology associated with disease and potentially limit the spread of MDRTB.

Thus, there is an urgent need for new more effective therapeutic regimens for active *M. tuberculosis* infections that increase treatment compliance by reducing the treatment time in order to decrease TB transmission.

BRIEF SUMMARY

The present disclosure relates to methods of treating an active *M. tuberculosis* infection or an active infection resulting from reactivation of a latent infection in a mammal and to methods of improving the efficacy of chemotherapy regimens against active *M. tuberculosis* infection.

The present disclosure is based on the surprising discovery that an active *M. tuberculosis* (Mtb) infection can be effectively treated by a treatment regime comprising a therapeutic Mtb composition such as a therapeutic Mtb vaccine and chemotherapeutic agent effective against a *M. tuberculosis* infection, thereby shortening the chemotherapy time required for protection, reducing bacterial burden, and/or extending survival. Further, surprisingly, the inventors have discovered that the therapeutic Mtb composition when delivered during an active TB infection as an adjunct to antibiotic therapy can produce a beneficial immune response to *M. tuberculosis* that improves the efficacy of a chemotherapeutic regime to TB disease. The inventors further discovered that administration of a therapeutic Mtb composition such as a therapeutic vaccine during an active TB infection adjunctively with a chemotherapeutic agent effective against a *M. tuberculosis* infection stimulated a significantly more robust, high quality (polyfunctional), and durable $T_H1$-type CD4+ T cell response.

Therefore, in one aspect, there is provided a method for treating an active tuberculosis infection in a mammal, the method comprising the step of administering to a mammal having an active infection with tuberculosis (e.g., *M. tuberculosis*) a chemotherapy agent and an immunologically effective amount of a therapeutic vaccine wherein the vaccine comprises a pharmaceutical composition comprising an Mtb antigen or an immunogenic fragment thereof from a *Mycobacterium* species of the tuberculosis complex and an adjuvant.

It will be understood in this and related methods of the disclosure that at least one step of administering the therapeutic vaccine, typically the initial step of administering the therapeutic vaccine, will take place when the mammal is actively infected with *M. tuberculosis* and/or exhibits at least one clinical symptom or positive assay result associated with active infection. It will also be understood that the methods of the present disclosure may further comprise additional steps of administering the same or another therapeutic vaccine of the present disclosure at one or more additional time points thereafter, irrespective of whether the active infection or symptoms thereof are still present in the mammal, and irrespective of whether an assay result associated with active infection is still positive, in order to improve the efficacy of chemotherapy regimens. It will also be understood that the methods of the present disclosure may include the administration of the therapeutic vaccine either alone or in conjunction with other agents and, as such, the therapeutic vaccine may be one of a plurality of treatment components as part of a broader therapeutic treatment regime. Accordingly, the methods of the present disclosure advantageously improve the efficacy of a chemotherapy treatment regime for the treatment of an active tuberculosis infection.

In certain embodiments, the therapeutic vaccine comprises an isolated fusion polypeptide comprising a combination of two or more covalently linked *M. tuberculosis* antigens, or immunogenic fragments thereof, wherein the antigens are selected from the group consisting of Rv0164, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv3872, Rv3873, Rv1511 and Rv3875, and antigens having at least 90% identity to any of the foregoing sequences.

In a specific embodiment, the therapeutic vaccine comprises the ID93 fusion polypeptide, which comprises the antigens Rv2608, Rv3619, Rv3620 and Rv1813.

In another specific embodiment, the therapeutic vaccine comprises the ID93 fusion polypeptide, which comprises the antigens Rv2608, Rv3619, Rv3620 and Rv1813, wherein the sequences of the antigens are from *M. tuberculosis*. In a more specific embodiment, the ID93 fusion polypeptide comprises a sequence set forth in SEQ ID NO: 1, or a sequence having at least 90% identity thereto.

Also provided herein is a method for treating an active tuberculosis infection in a mammal, the method comprising the step of administering to a mammal having an active tuberculosis infection an immunologically effective amount of a therapeutic vaccine in conjunction with one or more chemotherapeutic agents, wherein the vaccine comprises a pharmaceutical composition comprising an isolated fusion polypeptide, wherein the fusion polypeptide comprises (a) a combination of antigen Rv3620, and Rv2608 from a *Mycobacterium* species of a tuberculosis complex and the antigens are covalently linked, or (b) a sequence having at least 90% identity to the combination of antigens.

Also provided herein is a method for treating an active tuberculosis infection in a mammal, the method comprising the step of administering to a mammal having an active tuberculosis infection an immunologically effective amount of a therapeutic vaccine in conjunction with one or more chemotherapeutic agents, wherein the vaccine comprises a pharmaceutical composition comprising an isolated fusion polypeptide, wherein the fusion polypeptide comprises (a) a combination of antigen Rv1813, Rv3620, and Rv2608 from a *Mycobacterium* species of a tuberculosis complex and the antigens are covalently linked, or (b) a sequence having at least 90% identity to the combination of antigens.

In certain embodiments, the active infection to be treated according to the disclosed methods is an active infection that is causing a clinical symptom of active TB in the mammal, selected from the group consisting of weakness, fever, chills, weight loss, anorexia and night sweats. In other embodiments, the active infection is causing a clinical symptom of pulmonary TB symptoms in the mammal, selected from the group consisting of persistent cough, thick mucus, chest pain and hemoptysis. In still other embodiments, the active infection is characterized by Mtb bacteria which proliferate, reproduce, expand or actively multiply at an exponential, logarithmic, or semilogrithmic rate in an organ of the mammal. In other more specific embodiments, the active infection is identified using an assay selected from the group consisting of an acid fast staining (AFS) assay; a bacterial culture assay, such as the BACTEC MGIT 960 assay; an IGR test, such as the QFT®-Gold test or the QFT®-Gold In-tube T SPOT™.TB test; a skin test, such as the TST Mantoux skin test (TST); and intracellular cytokine staining of whole blood or isolated PBMC following antigen stimulation.

It will be apparent that, in some embodiments, the active infection will be an active primary infection of *M. tuberculosis*, while in others it will result from reactivation of a latent infection of *M. tuberculosis*. In some embodiments, the mammal will be infected with a multidrug resistant (MDR) strain of *M. tuberculosis*. In other embodiments, the mammal will have been previously immunized with *Bacillus* Calmette-Guerin (BCG).

Certain embodiments of the disclosed methods include administration of one or more chemotherapeutic agents effective in treating a *M. tuberculosis* infection, such as isoniazid and/or rifampin. In some situations, the mammal is first administered one or more chemotherapeutic agents over a period of time and then administered the therapeutic vaccine. In other situations, the mammal is first administered the therapeutic vaccine and then administered one or more chemotherapeutic agents over a period of time. In still other situations, administration of the one or more chemotherapeutic agents and the therapeutic vaccine is initiated at the same time. Further still, it will be understood that when practicing the disclosed methods it may be desirable to administer the pharmaceutical composition and/or therapeutic vaccine to the mammal on multiple occasions, e.g., one or more subsequent times after the first administration.

In some embodiments, the therapeutic vaccine further comprises an adjuvant. In some embodiments, the adjuvant used in the therapeutic vaccine is a GLA adjuvant, such as a GLA adjuvant having the following structure:

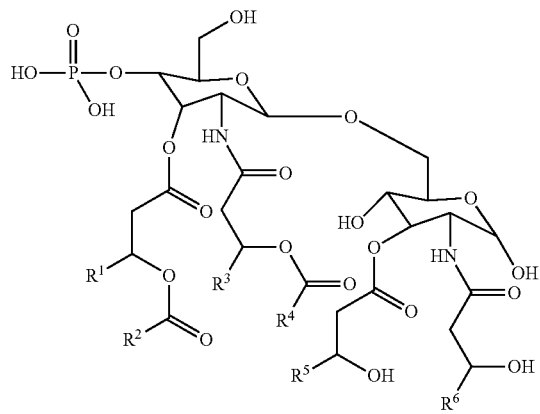

wherein $R^1$, $R^3$, $R^5$ and $R^6$ are $C_{11}$-$C_{20}$ alkyl; and $R^2$ and $R^4$ are $C_{12}$-$C_{20}$ alkyl or $C_9$-$C_{20}$ alkyl.

In a more specific embodiment, when using a GLA having the above structure, $R^1$, $R^3$, $R^5$ and $R^6$ are $C_{11-14}$ alkyl; and $R^2$ and $R^4$ are $C_{12-15}$ alkyl. In an even more specific embodiment, the GLA of the above structure is one in which $R^1$, $R^3$, $R^5$ and $R^6$ are $C_{11}$ alkyl; and $R^2$ and $R^4$ are $C_{13}$ alkyl. In an even more specific embodiment, the GLA of the above structure is one in which $R^1$, $R^3$, $R^5$ and $R^6$ are $C_{11}$ alkyl; and $R^2$ and $R^4$ are $C_9$ alkyl.

In another aspect, the compositions are employed in methods for reducing the time course of chemotherapy in an active tuberculosis infection in a subject, the method comprising the step of administering to a mammal with an active *Mycobacterium tuberculosis* infection an immunologically effective amount of a therapeutic vaccine as described herein, e.g., comprising a fusion protein or polypeptide or an immunogenic fragment thereof from a *Mycobacterium* species of the tuberculosis complex and an adjuvant, adjunctively with one or more chemotherapeutic agents effective against a *M. tuberculosis* infection, thereby reducing the time course of chemotherapy against a *M. tuberculosis* infection. In another aspect, provided herein is a method for reducing the time course of chemotherapy against an active tuberculosis infection, the method comprising administering to a mammal having an active tuberculosis infection an immunologically effective amount of a therapeutic vaccine in conjunction with the chemotherapy, wherein the vaccine comprises a pharmaceutical composition comprising an isolated fusion polypeptide, wherein the fusion polypeptide comprises (a) a combination of antigen Rv1813, Rv3620, and Rv2608 from a *Mycobacterium* species of a tuberculosis complex and the antigens are covalently linked, or (b) a sequence having at least 90% identity to the combination of antigens, and wherein the vaccine induces an immune response against tuberculosis, thereby providing for a reduced time course of the chemotherapy against an active tuberculosis infection. In some aspects, the time course of therapy is shortened to about 3, 4, 5, 6, or 7 months, e.g., no more than about 3, 4, 5, 6, or 7 months. By shortening the time course of chemotherapy against a *M. tuberculosis* infection, the present methods are also effective in enhancing the compliance of an individual being treated for an active *M. tuberculosis* infection in completing an entire course of treatment.

In a further aspect, the compositions are employed in methods for stimulating a polyfunctional, durable $T_H1$-type CD4+ T cell response in an active tuberculosis infection in a subject, the method comprising the step of administering to a mammal with an active *Mycobacterium tuberculosis* infection an immunologically effective amount of a therapeutic vaccine as described herein, e.g., comprising a fusion protein or an immunogenic fragment thereof from a *Mycobacterium* species of the tuberculosis complex and an adjuvant, adjunctively with one or more chemotherapeutic agents effective against a *M. tuberculosis* infection, thereby stimulating a polyfunctional, durable $T_H1$-type CD4+ T cell response. By shortening the time course of chemotherapy against a *M. tuberculosis* infection, the present methods are also effective in enhancing the compliance of an individual being treated for an active *M. tuberculosis* infection in completing an entire course of treatment.

In any of the aforementioned embodiments, a mammal may be a human.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1D shows the bacterial burden and survival of SWR/J and C57BL/6 mice infected with *Mycobacterium tuberculosis* (Mtb) and treated with antibiotics. SWR/J and C57BL/6 mice were infected with a low dose (50-100 bacteria) aerosol (LDA) of Mtb H37Rv (ATCC #27294). (FIG. 1A) The number of viable bacteria in the lungs (5 mice/group) were determined 15, 30 and 100 days after infection. Symbols indicate the mean+/−the standard deviation. (FIG. 1B) The survival of SWR/J and C57BL/6 mice was monitored in animals (8 mice/group) infected with Mtb H37Rv and mock- or treated with a 90-day antibiotic regimen (Rx 90d) consisting of INH and RIF administered on days 30-120. (FIG. 1C) SWR/J mice were infected with a LDA of Mtb H37Rv and treated with 30, 60 or 90 days of antibiotics starting on day 15 (Rx 30d, 60d, 90d) or on day 30 (Rx 90d (30)). Survival of SWR/J mice (7 mice/group) is shown. (FIG. 1D) Number of viable bacteria in the lungs of animals (5 mice/group) mock- or treated with a 90-day INH/RIF regimen (Rx 90d) administered on days 30-120, was determined 30, 60, 90, 120 and 150 days after infection. * P<0.05 (1-way ANOVA followed by Dunnett's Multiple Comparison Test or Logrank test) is considered significant. One representative of two experiments is shown.

FIG. 2B shows the colony-forming unit counts and survival of SWR/J mice infected with a LDA of Mtb and treated with antibiotics and ID93/GLA-SE. SWR/J mice were infected with LDA of Mtb (day 0). Fifteen days later (day 15) mice were mock- or antibiotics-treated for 90 days (Rx 90d). A subset of antibiotic-treated mice in each group was also immunized 3×3 weeks apart with ID93/GLA-SE either during (DTT; days 15, 36, 57) or post-antibiotic therapeutic treatment (PTT; days 107, 128, 149). (FIG. 2A) Scheme of immunotherapy experiments. (FIG. 2B) Number of viable bacteria in the lungs of animals (6 or 7 mice/group) was determined 177 days after infection. * P<0.05 is considered significant. (FIG. 2C) Protection was assessed by monitoring animal deaths (9 or 10 mice/group) caused by Mtb over time. One representative of four experiments is shown. P<0.05 (Logrank test) is considered significant.

FIG. 3A shows survival of SWR/J Mice infected with Mtb and treated with the ID93/GLA-SE vaccine and reduced antibiotic chemotherapy. SWR/J mice were infected with a LDA of Mtb H37Rv. Fifteen days later mice were treated for 60 or 90 days with antibiotics (Rx 60d and Rx 90, respectively). Following the completion of the 60 day antibiotic regimen, mice were immunized 3×3 weeks apart with ID93/GLA-SE. (FIG. 3A) Protection was assessed by monitoring animal deaths (7 mice/group) caused by Mtb over time. P<0.05 (Logrank test) is considered significant. (FIGS. 3B-3M) Histopathological evaluation of lung tissues post-challenge with Mtb H37Rv. Inflammatory responses and granuloma (g) formation are shown in H&E sections (FIGS. 3B-3I) and the presence of AFB (arrows) (FIGS. 3J-3M) was evaluated. (FIGS. 3B, 3F, 3J) Mock-treated mice, day 106; (FIGS. 3C, 3J and 3K) 90-day antibiotic therapy, day 106; (FIGS. 3D, 3H, 3L) 90-day antibiotic therapy+ID93/GLA-SE, day 241; (FIGS. 3E, 3I and 3M) 60-day antibiotic therapy+ID93/GLA-SE, day 295 Data shown are representative of 5 mice/group. One representative of three experiments is shown.

FIGS. 4A-4D shows ID93-specific cytokine responses in SWR mice following immunotherapy. SWR mice were infected with a LDA Mtb H37Rv and treated with either 90 days of antibiotics alone or antibiotics followed by immunization with ID93/GLA-SE 3×3 weeks apart. (FIG. 4A) Cytokine profile of ID93-stimulated splenocytes recovered at either day 177 or 241 post-infection. Cells were incubated for 24 hours in the presence of antigen or media control and supernatants were collected and analyzed by multiplex bead array for IFN-γ, IL-2, TNF, IL-5, IL-10, IL-13, and IL-17. Box plots show median and interquartile range after background subtraction. P-values from Wilcoxon rank sums test. (FIGS. 4B-4D) Intracellular cytokine staining for ID93-specific T-cell responses at days 149 and 177 post-infection. Cells were stimulated with ID93 or media control in the presence of brefeldin A for 8-12 hours, stained with fluorochrome-conjugated antibodies against CD3, CD4, CD8, CD44, IFN-γ, IL-2 and TNF. (FIGS. 4B and 4C) The panels show the gating scheme for FACS analysis. (FIG. 4D) Box plots in lower panel show median and interquartile range after background subtraction. P-values from Wilcoxon rank sums test. One representative of two experiments is shown.

FIGS. 5A-5D shows survival, clinical parameters and bacterial burden of Non-Human Primates (NHP) infected with Mtb and treated with antibiotics and ID 93/GLA-SE. Cynomolgus macaques were inoculated intratracheally with 1000 CFU of virulent *M. tuberculosis* (Erdman strain). The infection was allowed to proceed for 60 days followed by treatment with 30 days of INH/RIF antibiotics delivered by gavage or saline (Mock). Monkeys (7 per group) were injected with ID93/GLA-SE (Rx+ID93/GLA-SE) administered 3 times 2 weeks apart or did not receive further treatment (Mock, Rx). (FIG. 5A) Scheme of NHP immunotherapy experiment. (FIG. 5B) Survival was monitored for 50 weeks post exposure. (FIG. 5C) CYR changes were also evaluated monthly for 50 weeks post exposure. (FIG. 5D) At necropsy bacteria were quantified by enumerating the bacteriological burden (CFU) in monkey lungs. (FIG. 5E) Histologic appearance of H&E-stained sections of lung tissues harvested from NHP.

DETAILED DESCRIPTION

Figure 2A:
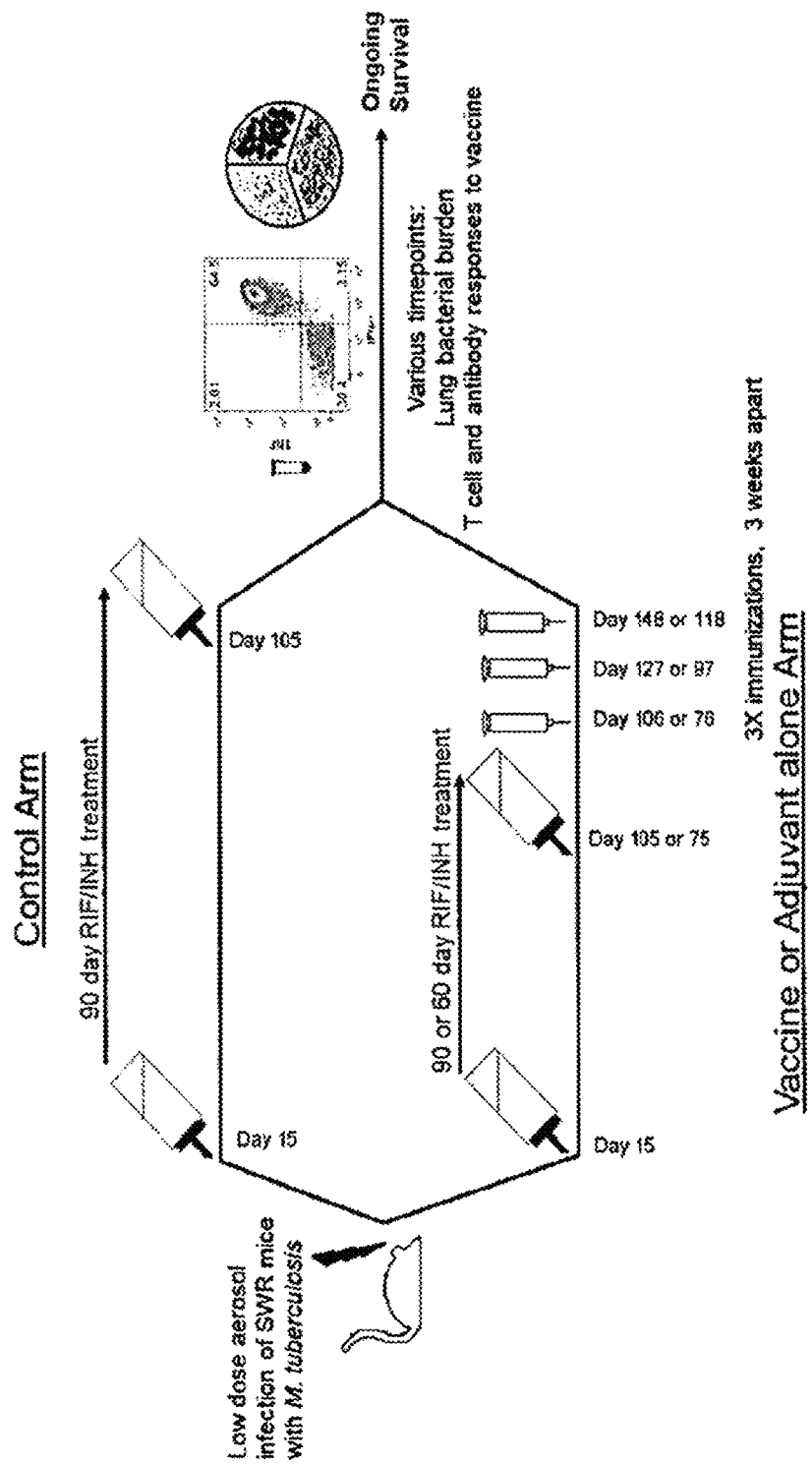

As described herein, the present disclosure relates generally to compositions and methods for treating active TB infection using therapeutic TB vaccines in combination with anti-TB chemotherapeutic agents, which may lead to shortened treatment times, clearance of TB bacilli, and potentially limiting the spread of MDR-TB.

The therapeutic vaccine compositions of the present invention generally comprise at least two heterologous polypeptides of a *Mycobacterium* species of the tuberculosis complex. A *Mycobacterium* species of the tuberculosis complex includes those species traditionally considered as causing the disease tuberculosis, as well as *Mycobacterium* environmental and opportunistic species that cause tuberculosis and lung disease in immune compromised patients, such as patients with AIDS, e.g., *Mycobacterium tuberculosis* (Mtb), *Mycobacterium bovis*, or *Mycobacterium africanum*, BCG, *Mycobacterium avium*, *Mycobacterium intracellulare*, *Mycobacterium celatum*, *Mycobacterium genavense*, *Mycobacterium haemophilum*, *Mycobacterium kansasii*, *Mycobacterium simiae*, *Mycobacterium vaccae*, *Mycobacterium fortuitum*, and *Mycobacterium scrofulaceum* (see, e.g., *Harrison's Principles of Internal Medicine*, volume 1, pp. 1004-1014 and 1019-1020). In a preferred embodiment, the *Mycobacterium* species to be prevented, treated or diagnosed according to the invention is *Mycobacterium tuberculosis* (Mtb). The sequences of antigens from *Mycobacterium* species are readily available. For example, *Mycobacterium tuberculosis* sequences can be found in Cole et al., Nature 393:533 (1998) and can be found at websites such as those maintained by the Wellcome Trust, Sanger Institute and Institut Pasteur.

In certain embodiments, the therapeutic vaccine comprises a fusion polynucleotide, fusion polypeptide, or composition, as described in US Patent Application Publication No. 2010/0129391 (the content of which are specifically incorporated herein by reference in its entirety).

For example, in certain specific embodiments, the therapeutic vaccine comprises an isolated fusion polypeptide or protein, or a polynucleotide encoding the same, comprising a combination of two or more covalently linked *Mycobacterium tuberculosis* antigens, or immunogenic fragments thereof, wherein the antigens are selected from the group consisting of Rv0164, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv3872, Rv3873, Rv1511 and Rv3875, and antigens having at least 90% identity to any of the foregoing sequences, as described in US Patent Application Publication No. 2010/0129391.

In some embodiments, the therapeutic vaccine comprises an isolated fusion polypeptide comprising (a) a combination of antigen Rv3620, and Rv2608 from a *Mycobacterium* species of a tuberculosis complex and the antigens are covalently linked, or (b) a sequence having at least 90% identity to the combination of antigens. In some embodiments, the therapeutic vaccine comprises an isolated fusion polypeptide comprising (a) a combination of antigen Rv1813, Rv3620, and Rv2608 from a *Mycobacterium* species of a tuberculosis complex and the antigens are covalently linked, or (b) a sequence having at least 90% identity to the combination of antigens. In some embodiments, the therapeutic vaccine comprises a fusion polypeptide comprising a combination of *Mycobacterium* antigens Rv2608, Rv3619, Rv3620 and Rv1813, or a sequence having at least 90% identity to the combination of antigens. In some embodiments, the *Mycobacterium* antigens Rv2608, Rv3619, Rv3620 and Rv1813 are *M. tuberculosis* antigens Rv2608, Rv3619, Rv3620 and Rv1813. hi some embodiments, the fusion polypeptide comprises a sequence set forth in SEQ ID NO: 1, or a sequence having at least 90% identity thereto. In some embodiments, the fusion polypeptide comprises a sequence set forth in SEQ ID NO:2, or a sequence having at least 90% identity thereto. In some embodiments, the therapeutic vaccine comprises a fusion polypeptide comprising a combination of *Mycobacterium* antigens Rv2608, Rv3620 and Rv1813, or a sequence having at least 90% identity the combination of antigens. In some embodiments, the *Mycobacterium* antigens Rv2608, Rv3620 and Rv1813 are *M. tuberculosis* antigens Rv2608, Rv3620 and Rv1813. In some embodiments, the fusion polypeptide comprises a sequence set forth in SEQ ID NO:3 or 4, or a sequence having at least 90% identity to SEQ ID NO:3 or SEQ ID NO:4. In some embodiments, antigen Rv1813 comprises the amino acid sequence of SEQ ID NO:5. In some embodiments, antigen Rv3620 comprises the amino acid sequence of SEQ ID NO:6. In some embodiments, antigen Rv2608 comprises the amino acid sequence of SEQ ID NO:7. In some embodiments, antigen Rv3619 comprises the amino acid sequence of SEQ ID NO:8. One skilled in the art would understand that one or more N-terminal amino acids (such as signal sequences) may be removed.

In a more specific embodiment, the therapeutic vaccine comprises the ID93 fusion protein, or a polynucleotide encoding the same, which comprises four antigens belonging to families of Mtb proteins associated with virulence (Rv2608, Rv3619, Rv3620) or latency (Rv1813), as described in US Patent Application Publication No. 2010/0129391 (specifically incorporated herein by reference in its entirety).

In some specific further embodiments, a fusion protein, e.g., an ID93 fusion protein, is formulated as a vaccine. In further specific embodiments, a therapeutic vaccine comprises a stable oil-in-water emulsion (SE) and GLA a synthetic TLR-4 agonist (GLA) as described in LIS Patent Application Publication No. 2008/0131466 (specifically incorporated herein by reference in its entirety). As one of ordinary skill in the art will understand, in some embodiments the therapeutic vaccine comprises an isolated polypeptide, an isolated fusion polypeptide or fragment (e.g., an antigenic/immunogenic portion) from a *Mycobacterium* species of the tuberculosis complex known in the art. Mtb polypeptides of the disclosure, antigenic/immunogenic fragments thereof, and other variants may be prepared using conventional recombinant and/or synthetic techniques.

In some embodiments, a nucleic acid molecule or fusion protein is administered with one or more chemotherapeutic agents effective against a *M. tuberculosis* infection. Examples of such chemotherapeutic agents include, but are not limited to, amikacin, aminosalicylic acid, capreomycin, cycloserine, ethambutol, ethionamide, isoniazid, kanamycin, pyrazinamide, rifamycins (i.e., rifampin, rifapentine and rifabutin), streptomycin, ofloxacin, ciprofloxacin, clarithromycin, azithromycin and fluoroquinolones. Such chemotherapy is determined by the judgment of the treating physician using preferred drug combinations. "First-line" chemotherapeutic agents used to treat a *M. tuberculosis* infection that is not drug resistant include isoniazid, rifampin, ethambutol, streptomycin and pyrazinamide. "Second-line" chemotherapeutic agents used to treat a *M. tuberculosis* infection that has demonstrated drug resistance to one or more "first-line" drugs and include but are not limited to ofloxacin, ciprofloxacin, ethionamide, aminosalicylic acid, cycloserine, amikacin, kanamycin and capreomycin.

In some embodiments, a therapeutic vaccine is administered to a mammal with active TB before, concurrently with, or after administration of the one or more chemotherapeutic agents effective against a *M. tuberculosis* infection. In some embodiments the chemotherapeutic is administered concurrently, at the same time. Alternatively, a chemotherapeutic is administered within minutes such as about 1, 5, 10, 15, 20, 25, 30, 35, 40, 45, 50 minutes, hours such as about 1, 3, 5, 7, 9, 11, 13, 15, 17, 19, 21, or even days such as about 1, 2, 3, 4, 5, or 6 days. In some embodiments, a chemotherapeutic is administered about 1, 2, 3, 4, 5, 6, 7, 8, 9, 10, 11 or 12 weeks before the therapeutic vaccine. In one embodiment, a nucleic acid molecule or fusion protein is administered about 2 weeks after commencing administration of one or more chemotherapeutic agents. The one or more chemotherapeutic agents are generally administered over a period of time, for example, for about 1, 2, 3, or 4 weeks, or about 2, 3, 4, 5, 6 or 8 months, or about 1 year or longer.

In some embodiments, a first administration in a mammal with an active TB infection of a therapeutic composition for stimulating an immune response comprising a nucleic acid molecule, fusion polypeptide, or vaccine is followed by one or more subsequent administrations of a nucleic acid, fusion polypeptide, or vaccine. For instance, a first administration with a nucleic acid molecule or fusion polypeptide is followed by one or more subsequent administrations of a nucleic acid molecule or fusion protein. In one embodiment, a first administration with a nucleic acid molecule or fusion polypeptide is followed by one or more subsequent administrations of a fusion polypeptide. In one embodiment, a first administration with a nucleic acid molecule or fusion polypeptide is followed by one or more subsequent administrations of a nucleic acid molecule. Usually the first or second or subsequent administrations are given about 2, 3, 4, 5, 6, 7, 8, 9, 10, 11, or 12 weeks apart, or up to about 4, 5, or 6 months apart. Further administrations are given about 6 months apart, or as long as 1, 2, 3, 4 or 5 years apart.

In another aspect, the compositions are employed in methods for reducing or shortening the time course of chemotherapy against a *M. tuberculosis* infection, the method comprising administering to a mammal already infected with *Mycobacterium tuberculosis* one or more chemotherapeutic agents effective against a *M. tuberculosis* infection and an immunologically effective amount of a pharmaceutical composition comprising a fusion polypeptide, e.g., ID93, or an immunogenic fragment thereof from a *Mycobacterium* species of the tuberculosis complex and an adjuvant, wherein said ID93 fusion polypeptide induces an immune response against *M. tuberculosis*, thereby allowing for reducing or shortening the time course of chemotherapy against a *M. tuberculosis* infection. Usually, administration of a nucleic acid molecule, fusion polypeptide, or vaccine will allow effective chemotherapeutic treatment against a *M. tuberculosis* infection within 6 months, 5 months, 4 months, 3 months, or less.

The compositions and methods of the present disclosure are usually administered to humans, but are effective in other mammals including domestic mammals (i.e., dogs, cats, rabbits, rats, mice, guinea pigs, hamsters, chinchillas) and agricultural mammals (i.e., cows, pigs, sheep, goats, horses).

Definitions

In the present description, the terms "about" and "consisting essentially of" mean+20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

A "chemotherapeutic", "chemotherapeutic agents" or "chemotherapy regime" is a drug or combination of drugs used to treat or in the treatment thereof of patients infected or exposed to any species of *M. tuberculosis* and includes, but is not limited to, amikacin, aminosalicylic acid, capreomycin, cycloserine, ethambutol, ethionamide, isoniazid (INH), kanamycin, pyrazinamide, rifamycins (i.e., rifampin, rifapentine and rifabutin), streptomycin, ofloxacin, ciprofloxacin, clarithromycin, azithromycin and fluoroquinolones and other derivatives analogs or biosimilars in the art. "First-line" chemotherapeutic agents are chemotherapeutic agents used to treat an *M. tuberculosis* infection that is not drug resistant and include but are not limited isoniazid, rifampin, ethambutol, streptomycin and pyrazinamide and other derivatives analogs or biosimilars in the art. "Second-line" chemotherapeutic agents used to treat a *M. tuberculosis* infection that has demonstrated drug resistance to one or more "first-line" drugs include without limitation ofloxacin, ciprofloxacin, ethionamide, aminosalicylic acid, cycloserine, amikacin, kanamycin and capreomycin and other derivatives analogs or biosimilars in the art.

As used herein "improving the efficacy of chemotherapy regimens" refers to shortening the duration of therapy required to achieve a desirable clinical outcome, reducing the number of different chemotherapeutics required to achieve a desirable clinical outcome, reducing the dosage of chemotherapeutics required to achieve a desirable clinical outcome, decreasing the pathology of the host or host organs associated with an active clinical infection, improving the viability of the host or organs of a host treated by the methods, reducing the development or incidence of MDR-TB strains, and/or increasing patient compliance with chemotherapy regimens.

A "therapeutic Mtb composition(s)" as used herein refers to a composition(s) capable of eliciting a beneficial immune response to *M. tuberculosis* when administered to a host with an active TB infection. A "beneficial immune response" is one that lessens signs or symptoms of active TB disease, reduces *bacillus* counts, reduces pathology associated with active TB disease, elicits an appropriate cytokine profile associated with resolution of disease, expands antigen specific CD4+ and CD8+ T cells, or improves the efficacy of chemotherapy regimens. Therapeutic Mtb compositions of the disclosure include without limitation polynucleotides which encode polypeptides, polypeptides, antigenic fragments, peptides, delivered in pharmaceutically acceptable formulations by methods known in the art and include vaccine formulations.

A "host", "subject", "patient", "mammal", or "individual" are all used herein interchangeably.

"*M. tuberculosis", "Mycobacterium tuberculosis*", "bacteria", "bacterium", "*bacillus*" as used herein all refer to the bacteria responsible for causing TB disease in a mammal.

A "drug resistant" *M. tuberculosis* infection refers to a *M. tuberculosis* infection wherein the infecting strain is not held static or killed (is resistant to) one or more of so-called "frontline" chemotherapeutic agents effective in treating a *M. tuberculosis* infection (e.g., isoniazid, rifampin, ethambutol, streptomycin and pyrazinamide).

A "multi-drug resistant", "MDR-TB" *M. tuberculosis* infection refers to a *M. tuberculosis* infection wherein the infecting strain is resistant to two or more of "front-line" chemotherapeutic agents effective in treating a *M. tuberculosis* infection. Multi-drug resistant *M. tuberculosis* infections as used herein also refer to "extensively drug-resistant tuberculosis" ("XDR-TB") as defined by the World Health Global task Force in October 2006 as a multi-drug resistant TB with resistance to any one of the fluoroquinolones (FQs) and at least one of the injectable drugs such as kanamycin, amikacin, and capreomycin.

"Active Tuberculosis", "Active TB", "TB Disease", "TB" or "Active Infection" as used herein refers to an illness, condition, or state in a mammal (e.g., a primate such as a human) in which Mtb bacteria are actively multiplying and invading organs of the mammal and causing symptoms or about to cause signs, symptoms or other clinical manifestations, most commonly in the lungs (pulmonary active TB) or can be due to an initial infection of the host. Clinical symptoms of active TB may include weakness, fatigue, fever, chills, weight loss, loss of appetite, anorexia, or night sweats. Pulmonary active TB symptoms include cough persisting for several weeks (e.g., at least 3 weeks), thick mucus, chest pain, and hemoptysis. "Reactivation tuberculosis" as used herein refers to active TB that develops in an individual having LTBI and in whom activation of dormant foci of infection results in actively multiplying Mtb bacteria. "Actively multiplying" as used herein refers to Mtb bacteria which proliferate, reproduce, expand or actively multiply at an exponential, logarithmic, or semilogrithmic rate in the organs of an infected host. In certain embodiments, an infected mammal (e.g., human) has a suppressed immune system. The immune suppression may be due to age (e.g., very young or older) or due to other factors (e.g., substance abuse, organ transplant) or other conditions such as another infection (e.g., HIV infection), diabetes (e.g., diabetes mellitus), silicosis, head and neck cancer, leukemia, Hodgkin's disease, kidney disease, low body weight, corticosteroid treatment, or treatments for arthritis (e.g., rheumatoid arthritis) or Crohn's disease, or the like.

Tests for determining the presence of active TB or condition caused by actively multiplying Mtb bacteria are known in the art and include but are not limited to Acid Fast Staining (AFS) and direct microscopic examination of sputum, bronchoalveolar lavage, pleural effusion, tissue biopsy, cerebrospinal fluid effusion; bacterial culture such as the BACTEC MGIT 960 (Becton Dickinson, Franklin Lakes, N.J., USA); IGR tests including the QFT®-Gold, or QFT®-Gold In-tube T SPOT™.TB, skin testing such as the TST The Mantoux skin test (TST); and intracellular cytokine staining of whole blood or isolated PBMC following antigen stimulation.

"Latent Tuberculosis Infection", "LTBI", "Latentcy", or "Latent Disease", "Dormant Infection", as used herein refers to an infection with *M. tuberculosis* (MTB) that has been contained by the host immune system resulting in a dormancy which is characterized by constant low bacterial numbers but may also contain at least a part of the bacterial population which remains in a state of active metabolism including reproduction at a steady maintenance state. Latent TB infection is determined clinically by a positive TST or IGRA without signs, symptoms or radiographic evidence of active TB disease. Latently infected mammals are not "contagious" and cannot spread disease due to the very low bacterial counts associated with latent infections. Latent tuberculosis infection (LTBI) is treated with a medication or medications to kill the dormant bacteria. Treating LTBI greatly reduces the risk of the infection progressing to active tuberculosis (TB) later in life (i.e., it is given to prevent reactivation).

"*Mycobacterium* species of the tuberculosis complex" includes those species traditionally considered as causing the disease tuberculosis, as well as *Mycobacterium* environmental and opportunistic species that cause tuberculosis and lung disease in immune compromised patients, such as patients with AIDS, e.g., *M. tuberculosis, M. bovis,* or *M. africanum,* BCG, *M. avium, M. intracellulare, M. celatum, M. genavense, M. haemophilum, M. kansasi, M. simiae, M. vaccae, M. fortuitum,* and *M. scrofulaceum* (see, e.g., Harrison's *Principles of Internal Medicine*, Chapter 150, pp. 953-966 (16th ed., Braunwald, et al., eds., 2005).

"Progressive Primary Tuberculosis" as used herein refers to a TB Disease that develops within the first several years after initial exposure to and infection with Mtb, due to failure of the host immune system to adequately contain the initial infection.

A "method of treatment", as disclosed herein, refers generally to a method for treating an active tuberculosis infection in a mammal using a therapeutic vaccine in conjunction with a chemotherapeutic treatment regime. It will be understood in this and related methods of the disclosure that at least one step of administering the therapeutic vaccine, typically the initial step of administering the therapeutic vaccine, will take place when the mammal is actively infected with *M. tuberculosis* and/or exhibits at least one clinical symptom or positive assay result associated with active infection. It will also be understood that the methods of the present disclosure may further comprise additional steps of administering the same or another therapeutic vaccine of the present disclosure at one or more additional time points thereafter, irrespective of whether the active infection or symptoms thereof are still present in the mammal, and irrespective of whether an assay result associated with active infection is still positive, in order to improve the efficacy of chemotherapy regimens. It will also be understood that the methods of the present disclosure may include the administration of the therapeutic vaccine either alone or in conjunction with other agents and, as such, the therapeutic vaccine may be one of a plurality of treatment components as part of a broader therapeutic treatment regime. Accordingly, the methods of the present disclosure advantageously improve the efficacy of a chemotherapy treatment regime for the treatment of an active tuberculosis infection.

Polypeptide Compositions

As noted, the present disclosure, in one aspect, provides isolated *Mycobacterium* polypeptides, as described herein, including fusion polypeptides, and compositions containing same, and their use in combination with chemotherapeutic agents for treating active TB infections. Generally, a polypeptide of the disclosure will be an isolated polypeptide and may be a fragment (e.g., an antigenic/immunogenic portion) from an amino acid sequence disclosed herein, or may comprise an entire amino acid sequence disclosed herein. Polypeptides of the disclosure, antigenic/immunogenic fragments thereof, and other variants may be prepared using conventional recombinant and/or synthetic techniques.

In certain embodiments, the polypeptides of the disclosure are antigenic/immunogenic, i.e., they react detectably within an immunoassay (such as an ELISA or T cell stimulation assay) with antisera and/or T cells from an infected subject. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present disclosure. An "immunogenic portion,-' as used herein, is a fragment of an immunogenic polypeptide of the disclosure that itself is immunologically reactive (i.e., specifically binds) with the B-cells and/or T cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T cell lines or clones. As used herein, antisera and antibodies are "antigen-specific" if they specifically bind to an antigen (i.e., they react with the protein in an immunoassay, and do not react detectably with unrelated proteins). Such antisera and antibodies may be prepared as described herein, and using well-known techniques.

In a particular embodiment, an antigenic/immunogenic portion of a polypeptide of the present disclosure is a portion that reacts with antisera and/or T cells at a level that is not substantially less than the reactivity of the full-length polypeptide (e.g., in an ELISA and/or T cell reactivity assay). Preferably, the level of immunogenic activity of the antigenic/immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having similar to or greater than about 100% or 150% or more immunogenic activity.

A polypeptide composition of the disclosure may also comprise one or more polypeptides that are immunologically reactive with T cells and/or antibodies generated against a polypeptide of the disclosure, particularly a polypeptide having an amino acid sequence disclosed herein, or to an immunogenic fragment or variant thereof.

In another embodiment of the disclosure, polypeptides are provided that comprise one or more polypeptides that are capable of eliciting T cells and/or antibodies that are immunologically reactive with one or more polypeptides described herein, or one or more polypeptides encoded by contiguous polynucleotide sequences contained in the polynucleotide sequences disclosed herein, or immunogenic fragments or variants thereof, or to one or more polynucleotide sequences which hybridize to one or more of these sequences under conditions of moderate to high stringency.

The present disclosure also provides polypeptide fragments, including antigenic/immunogenic fragments, comprising at least about 5, 10, 15, 20, 25, 50, or 100 contiguous amino acids, or more, including all intermediate lengths, of a polypeptide composition set forth herein, or those encoded by a polynucleotide sequence set forth herein.

In another aspect, the present disclosure provides variants of the polypeptide compositions described herein. Polypeptide variants (e.g., any of antigens and fusion polypeptides described herein) generally encompassed by the present disclosure will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequence set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the disclosure and evaluating their immunogenic activity as described herein using any of a number of techniques well known in the art.

For example, certain illustrative variants of the polypeptides of the disclosure include those in which one or more portions, such as an N-terminal leader sequence or transmembrane domain, have been removed. Other illustrative variants include variants in which a small portion (e.g., about 1-30 amino acids) has been removed from the N- and/or C-terminal of a mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present disclosure and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the disclosure, one skilled in the art will typically change one or more of the codons of the encoding DNA sequence according to Table A.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine K | Lys | K | AAA AAG |
| Leucine L | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Try | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5): valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within 0.2 is preferred, those within, 1 are particularly preferred, and those within, 0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0.1);

glutamate (+3.0.1); serine (+0.3); asparagine (+0.2); glutamine (+0.2); glycine (0); threonine (−0.4); proline (−0.5,1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within 2 is preferred, those within 0.1 are particularly preferred, and those within 0.0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the two sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Wash. D.C. Vol. 5, Suppl. 3, pp. 345-358; Hein J. (1990) *Unified Approach to Alignment and Phylogenes* pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) CABIOS 4:11-17; Robinson, E. D. (197 1) *Comb. Theor* 77:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Nat'lAcad., Sci. USA* 80:126-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'lAcad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In certain preferred embodiments of the disclosure, there are provided *Mycobacterium tuberculosis* fusion polypeptides, and polynucleotides encoding fusion polypeptides. Fusion polypeptide and fusion proteins refer to a polypeptide having at least two heterologous *Mycobacterium* sp. polypeptides, such as *Mycobacterium tuberculosis* polypeptides, covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. Fusion polypeptides or fusion proteins can also include conservatively modified variants, polymorphic variants, alleles, mutants, subsequences, interspecies homologs, and immunogenic fragments of the antigens that make up the fusion protein. *Mycobacterium tuberculosis* antigens are described in Cole et al., *Nature* 393:531 (1998), which discloses the entire *Mycobacterium tuberculosis* genome. Antigens from other *Mycobacterium* species that correspond to *Mycobacterium tuberculosis* antigens can be identified, e.g., using sequence comparison algorithms, as described herein, or other methods known to those of skill in the art, e.g., hybridization assays and antibody binding assays.

The fusion polypeptides of the disclosure generally comprise at least two antigenic polypeptides as described herein, and may further comprise other unrelated sequences, such as a sequence that assists in providing T helper epitopes (an immunological fusion partner), preferably T helper epitopes recognized by humans, or that assists in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques. Preferably, a fusion protein is expressed as a recombinant protein. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al. *Proc. Natl. Acad. Sci. USA* 83:8258 8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Within preferred embodiments, an immunological fusion partner for use in a fusion polypeptide of the disclosure is derived from protein D, a surface protein of the gramnegative bacterium *Haemophilus influenza* B (WO 91/18926). Preferably, a protein D derivative comprises approximately the first third of the protein (e.g., the first N-terminal 100 110 amino acids), and a protein D derivative may be lipidated. Within certain preferred embodiments, the first 109 residues of a lipoprotein D fusion partner is included on the N-terminus to provide the polypeptide with additional exogenous T cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS 1 (hemaglutinin). Typically, the N-terminal 81 amino acids are used, although different fragments that include T-helper epitopes may be used.

In another embodiment, an immunological fusion partner comprises an amino acid sequence derived from the protein known as LYTA, or a portion thereof (preferably a Cterminal portion). LYTA is derived from *Streptococcus pneumoniae*, which synthesizes an Nacetyl-Lalanine amidase known as amidase LYTA (encoded by the LytA gene; Gene 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 70:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Polynucleotide Compositions

The present disclosure, in another aspect, also provides isolated polynucleotides, particularly those encoding fusion polypeptides of this disclosure (e.g., ID93), as well as compositions comprising such polynucleotides. As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this disclosure can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present disclosure, and a polynucleotide may, but need not, be linked to other molecules and/or support materials. Polynucleotides may comprise a native sequence (i.e., an endogenous sequence that encodes a *Mycobacterium* antigen or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to the native protein. The effect on the immunogenicity of the encoded polypeptide may generally be assessed as described herein. The term "variants" also encompasses homologous genes of xenogenic origin.

In additional embodiments, the present disclosure provides isolated polynucleotides comprising various lengths of contiguous stretches of sequence identical to or complementary to one or more of the sequences disclosed herein. For example, polynucleotides are provided by this disclosure that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200 500; 500 1,000, and the like.

The polynucleotides of the present disclosure, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure, for example polynucleotides that are optimized for human and/or primate codon selection. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

*Mycobacterium* polynucleotides and fusions thereof may be prepared, manipulated and/or expressed using any of a variety of well-established techniques known and available in the art.

For example, polynucleotide sequences or fragments thereof which encode polypeptides of the disclosure, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present disclosure can be engineered using methods generally known in the art in order to alter polypeptide encoding sequences for a variety of reasons, including but not limited to, alterations which modify the cloning, processing, expression and/or immunogenicity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (1989), and Ausubel et al., *Current Protocols in Molecular Biology* (1989). A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic vims, TMV) or with bacterial expression vectors (e.g., Ti or pBR322 plasmids); or animal cell systems.

The "control elements" or "regulatory sequences" present in an expression vector are those non-translated regions of the vector-enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional $E.$ $coli$ cloning and expression vectors such as BLUESCRIPT (Stratagene), in which the sequence encoding the polypeptide of interest may be ligated into the vector in frame with sequences for the amino-terminal Met and the subsequent 7 residues of (3-galactosidase so that a hybrid protein is produced; pIN vectors (Van Heeke & Schuster, $J.$ $Biol.$ $Chem.$ 267:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, $Saccharomyces$ $cerevisiae,$ a number of vectors containing constitutive or inducible promoters such as alpha factor, alcohol oxidase, and PGH may be used. For reviews, see Ausubel et al. (supra) and Grant et al. $Methods$ $Enzymol.$ 753:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, $EMBO$ $J.$ <5:307-311 (1987)). Alternatively, plant promoters such as the small subunit of RUBISCO or heat shock promoters may be used (Coruzzi et al., EMBO J. 3:1671-1680 (1984); Broglie et al. $Science$ 224:838-843 (1984); and Winter et al. $Results$ $Probl.$ $Cell$ $Differ.$ 77:85-105 (1991)). These constructs can be introduced into plant cells by direct DNA transformation or pathogenmediated transfection. Such techniques are described in a number of generally available reviews (see, e.g., Hobbs in McGraw Hill, $Yearbook$ $of$ $Science$ $and$ $Technology,$ pp. 191-196 (1992)).

An insect system may also be used to express a polypeptide of interest. For example, in one such system, $Autographa$ $californica$ nuclear polyhedrosis virus (AcNPV) is used as a vector to express foreign genes in $Spodoptera$ $frugiperda$ cells or in $Trichoplusia$ larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, $S.$ $frugiperda$ cells or $Trichoplusia$ larvae in which the polypeptide of interest may be expressed (Engelhard et al., $Proc.$ $Natl.$ $Acad.$ $Sci.$ $U.S.A.$ 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a nonessential E1 or E3 region of the viral genome may be used to obtain a viable virus which is capable of expressing the polypeptide in infected host cells (Logan & Shenk, $Proc.$ $Natl.$ $Acad.$ $Sci.$ $U.S.A.$ 37:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, et al. $Results$ $Probl.$ $Cell$ $Differ.$ 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such posttranslational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77-.3567-70 (1980)); npt, which confers resistance to the aminoglycosides, neomycin and G-418 (ColbereGarapin et al., *J. Mol. Biol.* 750:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, (3-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotideencoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 758:1211-1216 (1983).

A wide variety of labels and conjugation techniques are known by those skilled in the ait and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the disclosure may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

In addition to recombinant production methods, polypeptides of the disclosure, and fragments thereof, may be produced by direct peptide synthesis using solid-phase techniques (Merrifield, *J. Am. Chem. Soc.* 55:2149-2154 (19631). Protein synthesis may be performed using manual techniques or by automation. Automated synthesis may be achieved, for example, using Applied Biosystems 43 1 A Peptide Synthesizer (Perkin Elmer). Alternatively, various fragments may be chemically synthesized separately and combined using chemical methods to produce the full length molecule.

Pharmaceutical and Vaccine Compositions

In another aspect, the present disclosure concerns formulations of one or more of the polynucleotide, polypeptide or other compositions disclosed herein in pharmaceutically-acceptable or physiologically-acceptable solutions for administration to a cell or an animal, either alone, or in combination with one or more other modalities of therapy. Such pharmaceutical compositions are particularly preferred for use as vaccines when formulated with a suitable immunostimulant/adjuvant system. The compositions are also suitable for use in a diagnostic context.

It will also be understood that, if desired, the compositions of the disclosure may be administered in combination with other agents as well, such as, e.g., other proteins or polypeptides or various pharmaceutically-active agents. There is virtually no limit to other components that may also be included, provided that the additional agents do not cause a significant adverse effect upon the objectives according to the disclosure.

In certain preferred embodiments the compositions of the disclosure are used as vaccines and are formulated in combination with one or more immuno stimulants. An immuno stimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this disclosure. For example, an adjuvant may be included. Many adjuvants contain a substance designed to protect the antigen from rapid catabolism, such as aluminum hydroxide or mineral oil, and a stimulator of immune responses, such as lipid A (natural or synthetic), Bortadella pertussis or *Mycobacterium* species or *Mycobacterium*-derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Other illustrative adjuvants useful in the context of the disclosure include Toll-like receptor agonists, such as TLR7 agonists, TLR7/8 agonists, and the like. Still other illustrative adjuvants include imiquimod, gardiquimod, resiquimod, and related compounds.

Certain preferred vaccines employ adjuvant systems designed to induce an immune response predominantly of the Th1 type. High levels of Th1-type cytokines (e.g., IFN-γ, TNF-αβ, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mossman & Coffman, *Ann. Rev. Immunol.* 7:145-173 (1989).

Certain adjuvants for use in eliciting a predominantly Th 1-type response include, for example, a combination of monophosphoryl lipid A, preferably 3-de-O-acylated monophosphoryl lipid A (3D-MPL™), together with an aluminum salt (U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immuno stimulatory DNA sequences are also described, for example, by Sato et al., Science 273:352 (1996). Another illustrative adjuvant comprises a saponin, such as Quil A, or derivatives thereof, including QS21 and QS7 (Aquila Biopharmaceuticals Inc, Framingham, Mass.); Escin; Digitonin; or *Gypsophila* or *Chenopodium quinoa* saponins. Other illustrative formulations include more than one saponin in the adjuvant combinations of the present disclosure, for example combinations of at least two of the following group comprising QS21, QS7, Quil A, 0-escin, or digitonin.

In other embodiments, the adjuvant is a glucopyranosyl lipid A (GLA) adjuvant, as described in U.S. Patent Application Publication No. 2008/0131466, the disclosure of which is incorporated herein by reference in its entirety. For example, in one embodiment, the GLA adjuvant used in the context of the present disclosure has the following structure:

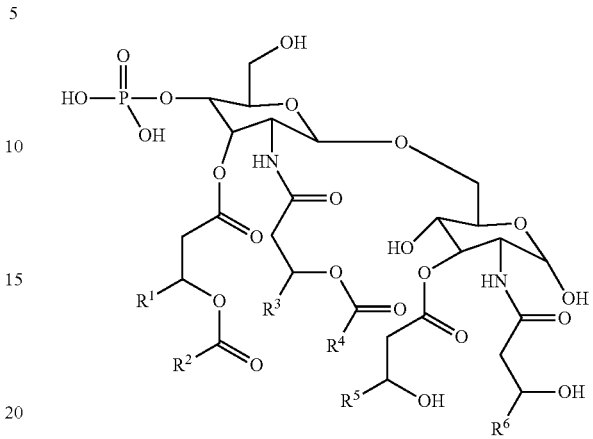

wherein $R^1$, $R^3$, $R^5$ and $R^6$ are $C_{11}$-$C_{20}$ alkyl and $R^2$ and $R^4$ are $C_{12}$-$C_{20}$ alkyl.

In a more specific embodiment, the GLA has the formula set forth above wherein $R^1$, $R^3$, $R^5$ and $R^6$ are Cu.m alkyl; and $R^2$ and $R^4$ are $C_{12}$-$C_{15}$ alkyl.

In a more specific embodiment, the GLA has the formula set forth above wherein $R^1$, $R^3$, $R^5$ and $R^6$ are $C_1$ alkyl; and $R^2$ and $R^4$ are $C_{13}$ alkyl.

In some embodiments, the adjuvant is a GLA adjuvant (e.g., synthetic) having the following structure:

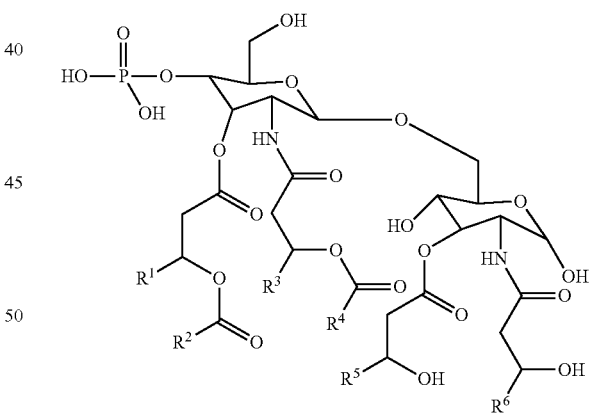

In certain embodiments of the above GLA structure, $R^1$, $R^3$, $R^5$ and $R^6$ are $C_1$-$C_{20}$ alkyl; and $R^2$ and $R^4$ are $C_9$-$C_{20}$ alkyl. In a more specific embodiment, $R^1$, $R^3$, $R^5$ and $R^6$ are $C_{11}$ alkyl; and $R^2$ and $R^4$ are $C_{13}$ alkyl. In another more specific embodiment, $R^1$, $R^3$, $R^5$ and $R^6$ are $C_{10}$ alkyl; and $R^2$ and $R^4$ are Q alkyl. In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the adjuvant is a GLA adjuvant (e.g., synthetic) having the following structure:

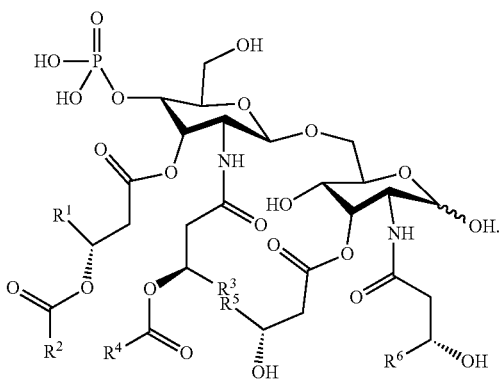

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the adjuvant is a synthetic GLA adjuvant having the following structure:

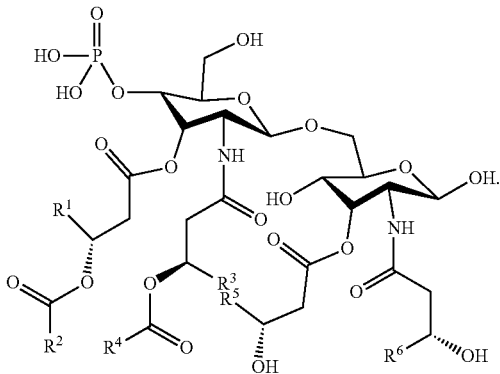

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the adjuvant is a synthetic GLA adjuvant having the following structure:

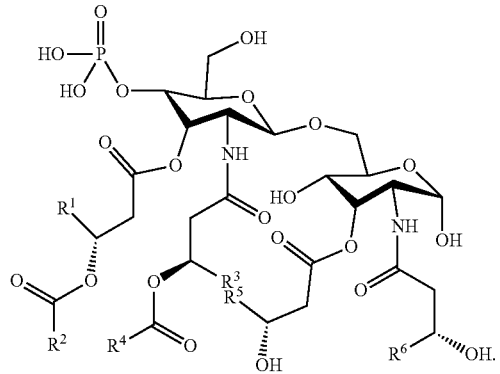

In certain embodiments of the above GLA structure, $R^1$, $R^3$, $R^5$ and $R^6$ are $C_1$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the adjuvant is a synthetic GLA adjuvant having the following structure:

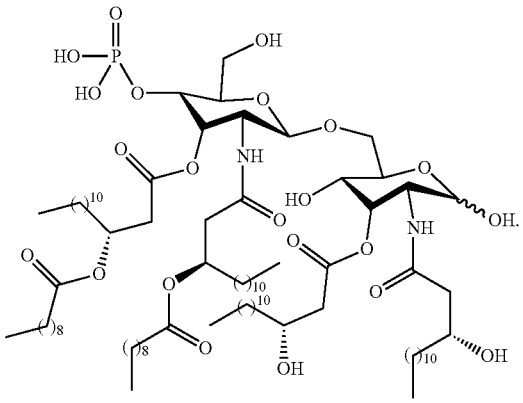

In certain embodiments, the adjuvant is a synthetic GLA adjuvant having the following structure:

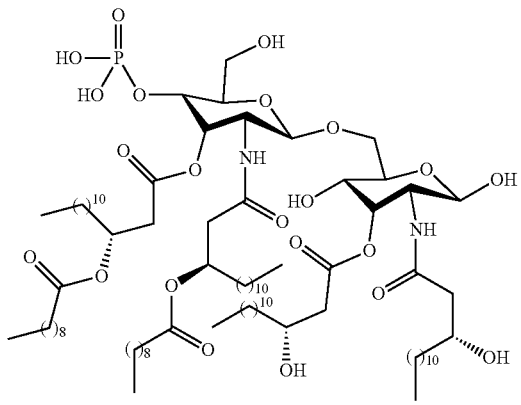

In certain embodiments, the adjuvant is a synthetic GLA adjuvant having the following structure:

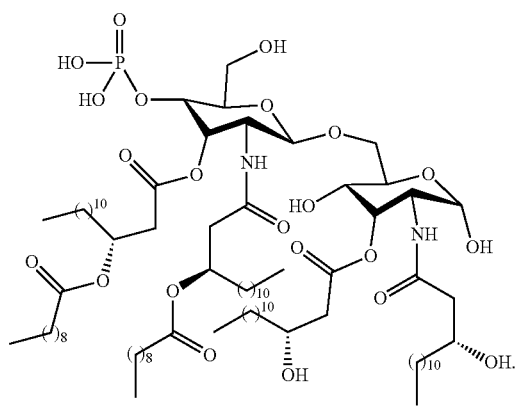

In a particular embodiment, the adjuvant system includes the combination of a monophosphoryl lipid A and a saponin derivative, such as the combination of QS21 and 3DMPL™. adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3DMPL™ adjuvant and tocopherol in an oil-in-water emulsion is described in WO 95/17210.

Another enhanced adjuvant system involves the combination of a CpG-containing oligonucleotide and a saponin derivative as disclosed in WO 00/09159. Other illustrative adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox, RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Compositions of the disclosure may also, or alternatively, comprise T cells specific for a *Mycobacterium* antigen. Such cells may generally be prepared in vitro or ex vivo, using standard procedures. For example, T cells may be isolated from bone marrow, peripheral blood, or a fraction of bone marrow or peripheral blood of a patient. Alternatively, T cells may be derived from related or unrelated humans, non-human mammals, cell lines or cultures.

T cells may be stimulated with a polypeptide of the disclosure, polynucleotide encoding such a polypeptide, and/or an antigen presenting cell (APC) that expresses such a polypeptide. Such stimulation is performed under conditions and for a time sufficient to pennit the generation of T cells that are specific for the polypeptide. Preferably, the polypeptide or polynucleotide is present within a delivery vehicle, such as a microsphere, to facilitate the generation of specific T cells.

T cells are considered to be specific for a polypeptide of the disclosure if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the disclosure (100 ng/ml-100 g/ml, preferably 200 ng/ml-25 µg/ml) for 3-7 days should result in at least a two-fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

In the pharmaceutical compositions of the disclosure, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologies standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present disclosure into suitable host cells. In particular, the compositions of the present disclosure may be formulated for delivery either encapsulated in a lipid particle, a liposome, a vesicle, a nanosphere, a nanoparticle or the like. The formulation and use of such delivery vehicles can be carried out using known and conventional techniques.

Exemplar Embodiments

1. A method for treating an active tuberculosis infection in a mammal, the method comprising the step of administering to a mammal having an active tuberculosis infection a chemotherapy agent and an immunologically effective amount of a therapeutic vaccine, wherein the vaccine comprises a pharmaceutical composition comprising an Mtb antigen or an immunogenic fragment thereof from a *Mycobacterium* species of a tuberculosis complex.

2. The method of embodiment 1, wherein the therapeutic vaccine comprises an isolated fusion polypeptide comprising a combination of two or more covalently linked *Mycobacterium tuberculosis* antigens, or immunogenic fragments thereof, wherein the antigens are selected from the group consisting of Rv0164, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv3872, Rv3873, Rv1511 and Rv3875, and antigens having at least 90% identity to any of the foregoing sequences.

3. The method of embodiment 1, wherein the therapeutic vaccine comprises an ID93 fusion polypeptide, wherein the ID93 fusion polypeptide comprises *Mycobacterium* antigens Rv2608, Rv3619, Rv3620 and Rv1813.

4. The method of embodiment 3, wherein the *Mycobacterium* antigens Rv2608, Rv3619, Rv3620 and Rv1813 are *M. tuberculosis* antigens Rv2608, Rv3619, Rv3620 and Rv1813.

5. The method of embodiment 3, wherein the ID93 fusion polypeptide comprises a sequence set forth in SEQ ID NO: 1, or a sequence having at least 90% identity thereto.

6. The method of embodiment 1, wherein the active tuberculosis infection is associated with a clinical symptom of weakness, fatigue, fever, chills, weight loss, loss of appetite, anorexia, night sweats, or any combination thereof.
7. The method of embodiment 1, wherein the active tuberculosis infection is a pulmonary active TB infection.
8. The method of embodiment 7, wherein the pulmonary active tuberculosis infection is associated with a clinical symptom of persistent cough, thick mucus, chest pain, hemoptysis, or any combination thereof.
9. The method of embodiment 1, wherein the active tuberculosis infection is characterized by Mtb bacteria which proliferate, reproduce, expand or actively multiply at an exponential, logarithmic, or semilogrithmic rate in an organ of the mammal.
10. The method of embodiment 1, wherein the active tuberculosis infection is identified using an assay selected from the group consisting of an acid fast staining (AFS) assay; a bacterial culture assay, such as the BACTEC MGIT 960 assay; an IGR test, such as the QFT®-Gold test or the QFT®-Gold In-tube T SPOT™.TB test; a skin test, such as the TST Mantoux skin test (TST); and intracellular cytokine staining of whole blood or isolated PBMC following antigen stimulation.
11. The method of embodiment 1, wherein the active tuberculosis infection is an active primary infection of *M. tuberculosis*.
12. The method of embodiment 1, wherein the active tuberculosis infection is a reactivation tuberculosis infection.
13. The method of embodiment 1, wherein the mammal is infected with a multidrug resistant (MDR) *M. tuberculosis*.
14. The method of embodiment 1, wherein the mammal was previously immunized with *Bacillus* Calmette-Guerin (BCG).
15. The method of embodiment 1, wherein the mammal is a human.
16. The method of embodiment 1, further comprising the administration of one or more chemotherapeutic agents effective in treating a *M. tuberculosis* infection.
17. The method of embodiment 16, wherein the one or more chemotherapeutic agents is isoniazid, rifampin, or a combination thereof.
18. The method of embodiment 16, wherein the mammal is first administered one or more chemotherapeutic agents over a period of time and subsequently administered the therapeutic vaccine.
19. The method of embodiment 16, wherein the mammal is first administered the therapeutic vaccine and subsequently administered one or more chemotherapeutic agents over a period of time.
20. The method of embodiment 16, wherein administration of the one or more chemotherapeutic agents and the therapeutic vaccine is concurrent.
21. The method of embodiment 1, further comprising administering the therapeutic vaccine to the mammal one or more subsequent times, wherein a tuberculosis infection remaining in the mammal at the one or more subsequent times may or may not be an active tuberculosis infection.
22. The method of embodiment 1, wherein the vaccine further comprises an adjuvant.
23. The method of embodiment 22, wherein the adjuvant is GLA, having the following structure:

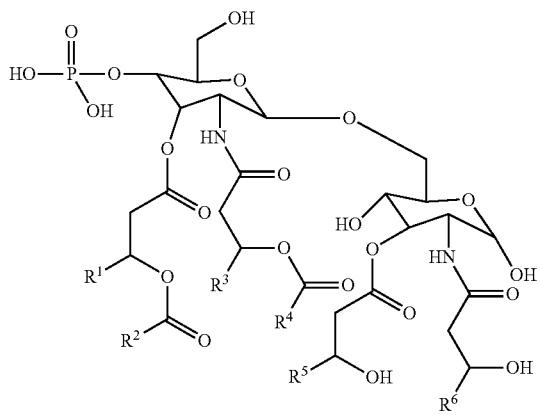

wherein $R^1$, $R^3$, $R^5$ and $R^6$ are $C_{11}$-$C_{20}$ alkyl; and $R^2$ and $R^4$ are $C_{12}$-$C_{20}$ alkyl.
24. The method of embodiment 23, wherein $R^1$, $R^3$, $R^5$ and $R^6$ are $C_1$-$C_{14}$ alkyl; and $R^2$ and $R^4$ are $C_{12}$-$C_{15}$ alkyl.
25. The method of embodiment 23, wherein $R^1$, $R^3$, $R^5$ and $R^6$ are $C_{11}$ alkyl; and $R^2$ and $R^4$ are $C_{13}$ alkyl.
26. A method for reducing the time course of chemotherapy against an active tuberculosis infection, the method comprising administering to a mammal having an active tuberculosis infection one or more chemotherapeutic agents effective against *M. tuberculosis* and an immunologically effective amount of a therapeutic vaccine, where the vaccine comprises a pharmaceutical composition comprising a fusion polypeptide or a immunogenic fragment thereof from a *Mycobacterium* species of a tuberculosis complex, and wherein the fusion polypeptide induces an immune response against *M. tuberculosis*, thereby providing for a reduced time course of chemotherapy against an active *M. tuberculosis* infection.
27. The method of embodiment 26, wherein the fusion polypeptide comprises a combination of two or more covalently linked *Mycobacterium tuberculosis* antigens, or immunogenic fragments thereof, wherein the antigens are selected from the group consisting of Rv0164, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv3872, Rv3873, Rv1511 and Rv3875, and antigens having at least 90% identity to any of the foregoing sequences.
28. The method of embodiment 27, wherein the fusion polypeptide comprises the ID93 fusion polypeptide, which comprises the antigens Rv2608, Rv3619, Rv3620 and Rv1813.
29. The method of embodiment 28, wherein the ID93 fusion polypeptide comprises a sequence set forth in SEQ ID NO: 1, or a sequence having at least 90% identity thereto.
30. The method of embodiment 26, wherein time course of chemotherapy is shortened to no more than about 3 months, about 5 months, or about 7 months.
31. The method of embodiment 26, wherein the vaccine further comprises an adjuvant.
32. The method of embodiment 31, wherein the adjuvant is GLA, having the following structure:

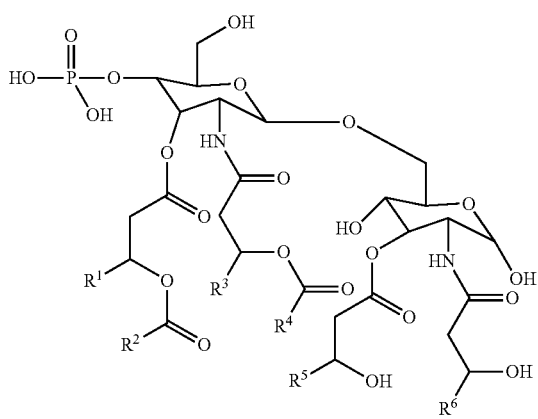

wherein $R^1$, $R^3$, $R^5$ and $R^6$ are $C_{11}$-$C_{20}$ alkyl; and $R^2$ and $R^4$ are $C_{12}$-$C_{20}$ alkyl.

33. The method of embodiment 32, wherein $R^1$, $R^3$, $R^5$ and $R^6$ are $C_{11}$-$C_{14}$ alkyl; and $R^2$ and $R^4$ are $C_{12}$-$C_{15}$ alkyl.

34. The method of embodiment 32, wherein $R^1$, $R^3$, $R^5$ and $R^6$ are $C_{11}$ alkyl; and $R^2$ and $R^4$ are $C_{13}$ alkyl.

35. A method for treating a patient diagnosed with an active tuberculosis infection, the method comprising administering to the patient a chemotherapy agent and an immunologically effective amount of a therapeutic vaccine, wherein the vaccine comprises a pharmaceutical composition comprising an Mtb antigen or an immunogenic fragment thereof from a *Mycobacterium* species of a tuberculosis complex.

36. The method of embodiment 35, wherein the patient is human.

37. The method of embodiment 35, wherein the therapeutic vaccine comprises an isolated fusion polypeptide comprising a combination of two or more covalently linked *Mycobacterium tuberculosis* antigens, or immunogenic fragments thereof, wherein the antigens are selected from the group consisting of Rv0164, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv3872, Rv3873, Rv1511 and Rv3875, and antigens having at least 90% identity to any of the foregoing sequences.

38. The method of embodiment 35, wherein the therapeutic vaccine comprises an ID93 fusion polypeptide, wherein the ID93 fusion polypeptide comprises *Mycobacterium* antigens Rv2608, Rv3619, Rv3620 and Rv1813.

39. The method of embodiment 38, wherein the *Mycobacterium* antigens Rv2608, Rv3619, Rv3620 and Rv1813 are *M. tuberculosis* antigens Rv2608, Rv3619, Rv3620 and Rv1813.

40. The method of embodiment 38, wherein the ID93 fusion polypeptide comprises sequence set forth in SEQ ID NO:1, or a sequence having at least 90% identity thereto.

41. The method of embodiment 35, wherein the active tuberculosis infection I associate with a clinical symptom of weakness, fatigue, fever, chills, weight loss, loss of appetite anorexia, night sweats, or any combination thereof.

42. The method of claim 35, wherein the active tuberculosis infection is a pulmonary active TB infection.

43. The method of embodiment 42, wherein the pulmonary active tuberculosis infection is associated with a clinical symptom of persistent cough, thick mucus, chest pain hemoptysis, or any combination thereof.

44. The method of embodiment 35, wherein the active tuberculosis infection I characterized by Mtb bacteria which proliferate, reproduce, expand or actively multiply at a exponential, logarithmic, or semilogrithmic rate in an organ of the patient.

45. The method of embodiment 35, wherein the active tuberculosis infection is identified using an assay selected from the group consisting of an acid fast staining (AFS) assay; a bacterial culture assay, such as the BACTEC MGIT 960 assay; an IGR test, such as the QFT®-Gold test or the QFT®-Gold In-tube T SPOT™.TB test; a skin test, such as the TST Mantoux skin test (TST); and intracellular cytokine staining of whole blood or isolate PBMC following antigen stimulation.

46. The method of embodiment 35, wherein the active tuberculosis infection is an active primary infection of *M. tuberculosis*.

47. The method of embodiment 35, wherein the active tuberculosis infection is reactivation tuberculosis infection.

48. The method of embodiment 35, wherein the patient is infected with a multidrug resistant (MDR) *M. tuberculosis*.

49. The method of embodiment 35, wherein the patient was previously immunized wit *Bacillus* Calmette-Guerin (BCG).

50. The method of embodiment 35, wherein the patient is a mammal.

51. The method of embodiment 35, further comprising the administration of one or more chemotherapeutic agents effective in treating a *M. tuberculosis* infection.

52. The method of embodiment 51, wherein the one or more chemotherapeutic agents is isoniazid, rifampin, or a combination thereof.

53. The method of embodiment 51, wherein the patient is first administered one or more chemotherapeutic agents over a period of time and subsequently administered the therapeutic vaccine.

54. The method of embodiment 51, wherein the patient is first administered the therapeutic vaccine and subsequently administered one or more chemotherapeutic agent over a period of time.

55. The method of embodiment 51, wherein administration of the one or more chemotherapeutic agents and the therapeutic vaccine is concurrent.

56. The method of embodiment 35, further comprising administering the therapeutic vaccine to the patient one or more subsequent times, wherein a tuberculosis infection remaining in the patient at the one or more subsequent times may or may not be an active tuberculosis infection.

57. The method of embodiment 35, wherein the vaccine further comprises an adjuvant.

58. The method of embodiment 57, wherein the adjuvant is GLA, having the following structure:

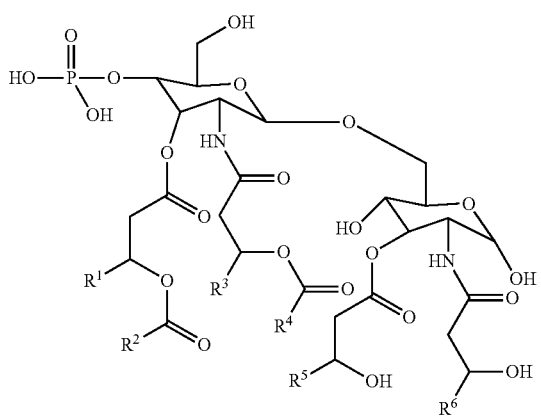

wherein $R^1$, $R^3$, $R^5$ and $R^6$ are $C_{11}$-$C_{20}$ alkyl; and $R^2$ and $R^4$ are $C_{12}$-$C_{20}$ alkyl.

59. The method of embodiment 58, wherein $R^1$, $R^3$, $R^5$ and $R^6$ are $C_{11}$-$C_{14}$ alkyl; and $R^2$ and $R^4$ are $C_{12}$-$C_{15}$ alkyl.
60. The method of embodiment 58, wherein $R^1$, $R^3$, $R^5$ and $R^6$ are $C_{11}$ alkyl; and $R^2$ an $R^4$ are $C_{13}$ alkyl.

The following Examples are offered by way of illustration and not by way of limitation.

Example 1

Development of the SWR/J Mouse Model of TB Relapse and Reactivation of an Active TB Infection Female, age-matched (4-6 weeks) SWR/J and C57BL/6 mice were purchased from Jackson and Charles River Laboratories, respectively. Mice were infected with a low dose (50-100 bacteria) aerosol (LDA) of Mtb H37Rv (ATCC #35718) using a UW-Madison aerosol chamber. The number of bacilli present in mice with an active infection the number of viable bacteria in the lungs (5 mice/group) were determined 15, 30 and 100 days after infection by methods known in the art. Symbols indicate the mean+/−the standard deviation. SWR/J and C57BL/6 strains with an active TB infection, mice were infected with Mtb H37Rv as described (8 mice/group) and survival monitored. To access the effect of chemotherapeutics on the model, fifteen days post-infection, a subset of mice were started on a drug regimen of isoniazid (INH) (at 85 mg/L of drinking water) and rifampin (RIF) (at 50 mg/L of drinking water) administered for 30, 60 or 90 consecutive days (Rx 30d, Rx 60d, Rx 90d). An additional group of mice were started on a drug regimen of isoniazid (INH) (at 85 mg/L of drinking water) and rifampin (RIF) (at 50 mg/L of drinking water) (collectively herein referred to as chemotherapeutic treatment) at 30 days post infection administered for 90 consecutive days. Female mice are estimated to drink between 0.15 and 0.37 mL/g (Bachmanov A A et al., 2002) The minimum inhibitory concentrations for Mtb H37Rv are 0.25 µM for RIF and 1.0 LpM for INH.

In contrast to C57BL/6 mice (Russell, et al., 2010), and consistent with previous observations (Baldwin et al., *J of Immunology* 2012), SWR/J mice failed to transition to a chronic state after Mtb infection as indicated by increasing viral titers in the SWR/J compared to the C57BL/6 mice (FIG. 1A) and are representative of a model of active MTB infection. Mock-treated SWR/J mice succumbed to lethal Mtb infection with a median survival time (MST) of 116.5 days, while those treated with chemotherapeutics (RIF/INH) for 90 days had an MST of 247.5 days (P<0.001; Logrank test) compared to mock or chemotherapeutic treated $C_{57}$/BL/6 mice (FIG. 1B).

To determine optimal length of chemotherapeutic treatment in the SWR/J mice, animals were treated with RIF/INH beginning on day 15 post infection for either 30, 60, or 90 days or an additional group that received chemotherapy beginning on day 30 post exposure for 90 days. Survival curves were monitored. Significant differences in survival and recoverable lung CFU between animals that were mock- or drug-treated for 30 (P<0.0005; Logrank test), 60 (P<0.05; Logrank test) or 90 days (P<0.005; Logrank test) were observed (FIG. 1C). Changing the initiation of chemotherapy from 15 to 30 days post-infection did not significantly alter the long term efficacy of treatment (P>0.50; Logrank test) (FIG. 1C). While 60 or 90 days of chemotherapy was sufficient to decrease the number of viable lung bacteria below the limit of detection (FIG. 1D), these treatment regimens were insufficient to achieve clearance of Mtb in SWR/J mice.

Example 2

Evaluation of Therapeutic Efficacy of the TB Vaccine ID93+Chemotherapy in the SWR/J Mouse Model of TB Relapse and Reactivation of an Active TB Infection TB vaccine fusion proteins ID83 and ID93 or their component antigens formulated with the TLR4 antagonist GLA-SE have been previously demonstrated to provide prophylactic protection against TB in mouse and guinea pig, models when administered in three doses (Baldwin, et. al. 2009, Bertholet et al., 2010). The ID93/GLA-SE vaccine was tested in the SWR/J model of active infection to determine if this formulation would provide immunotherapeutic benefit as measured by reduction of CFU or improved survival. SWR/J mice (6 or 7 mice per group) were infected with LDA of Mtb as described in Example 1. Fifteen days later (day 15) mice were mock- or antibiotics-treated for 90 days (Rx 90d). A subset of antibiotic-treated mice in each group were also immunized. Mice were immunized 3 times, 3 weeks apart with 8 µg of ID93protein formulated with 20 µg of GLA-SE either during (DTT; days 15, 36, 57) or post-antibiotic therapeutic treatment (PTT; days 107, 128, 149). Therapeutic efficacy was determined by tracking survival over time and by plating lung homogenates as previously described (Bertholet et al., 2008). The ID93/GLA-SE vaccine administered therapeutically(- -) in the SWR/J mice model of active TB infection increased the frequency of survival after infection (P<0.01).

Figures 2B, 2C:
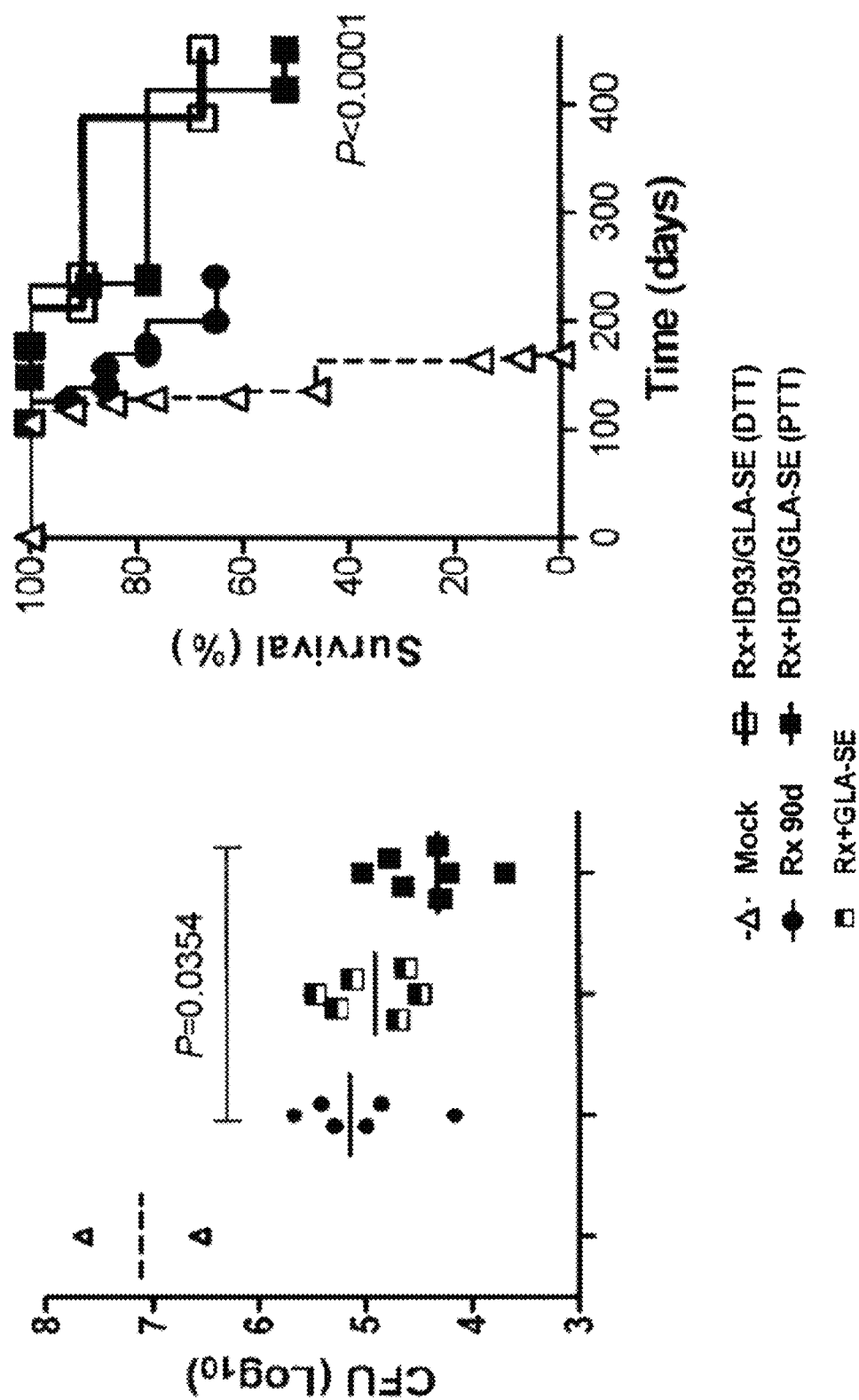

Compared to chemotherapy (Rx) alone (-●-), immunization with the ID93/GLA-SE vaccine as an adjunct to chemotherapy (-■-) further reduced CFU by 0.643 log 10 (P<0.05) (FIG. 2B). No differences in lung CFU were observed between the groups administered GLASE adjuvant alone plus chemotherapy (Rx+GLA-SE (-■-)), compared to chemotherapy alone Rx (-●-) (P>0.05) (FIG. 2B). Moreover, there was a significant difference between the post-exposure efficacy induced by the Rx+ID93/GLA-SE and the Rx+GLA-SE groups (4.419+0.17 vs. 4.938+0.16 $log_{10}$, P<0.05), demonstrating that the adjunctive bactericidal effect observed in these studies is antigen dependent.

Administration of the vaccine as an immunotherapeutic adjunct to chemotherapy after (PTT) or during (DTT) 90 days of chemotherapy treatment prevented death in 52% and 67% of Mtb-infected mice, respectively, (P<0.0001) (FIG. 2C).

Example 3

Figure 3A:
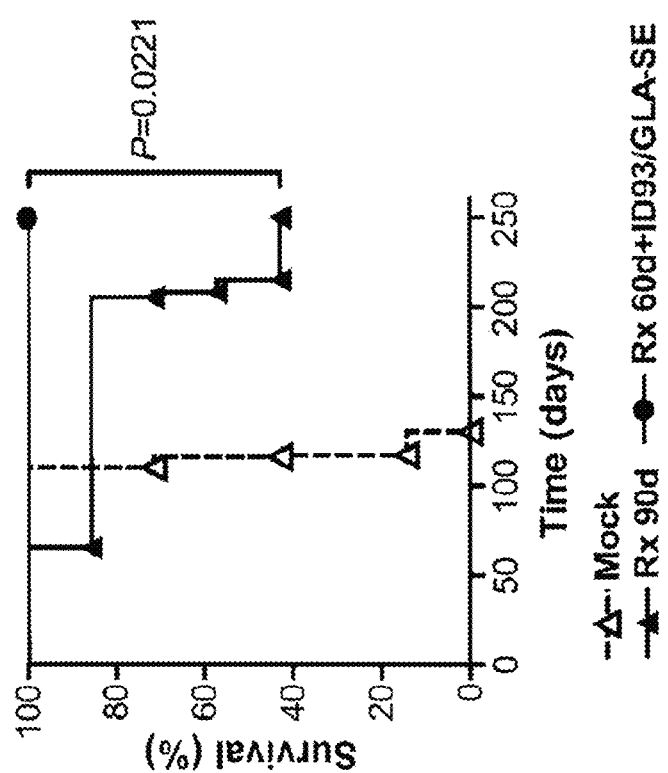
Figure 3B:
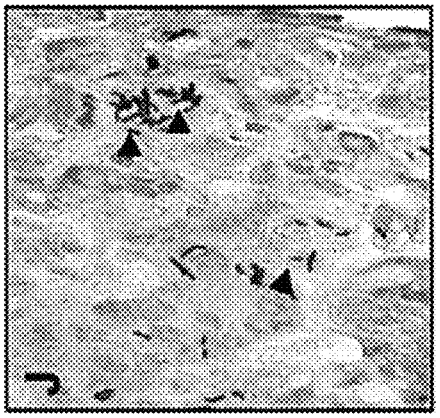
Figure 3F:
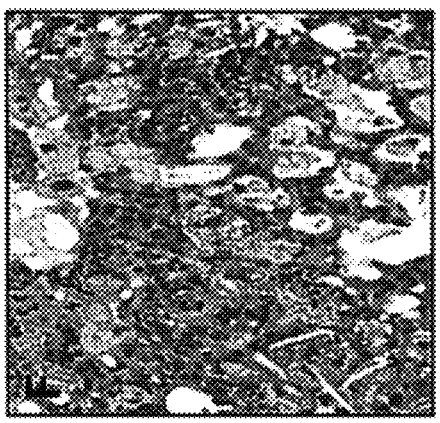

Administration of the Therapeutic ID93/GLA-SE Vaccine as an Adjunct to Chemotherapy Reduces the Duration of Drug Therapy Required to Prolong Survival in an Active TB Infection Additional experiments were performed in the SWR/J mouse model of TB relapse and reactivation of an active TB infection to evaluate if administration of the therapeutic ID93/GLASE vaccine could reduce the duration of drug therapy required to prolong survival in an active TB infection. SWR/J mice were infected with a LDA of Mtb H37Rv. Fifteen days later mice were treated for 60 or 90 days with antibiotics as previously described (Rx 60d and Rx 90, respectively). Following the completion of the 60 day antibiotic regimen, mice were immunized immunized 3 times, 3 weeks apart with 8 μg of ID93 protein formulated with 20 μg of GLASE(Rx 60d+ID93/GLA-SE; days 77, 98, 119). Protection was assessed by monitoring animal deaths (7 mice/group) caused by Mtb over time (P<0.05 (Logrank test) is considered significant). (B-M) Histopathological evaluation of lung tissues post-challenge with Mtb H37Rv. Inflammatory responses and granuloma (g) formation are shown in H&E sections (B-I) and the presence of AFB (arrows) (J-M) was evaluated. (B, F, J) Mock-treated mice, day 106; (C, J and K) 90-day antibiotic therapy, day 106; (D, H, L) 90-day antibiotic therapy+ID93/GLA-SE, day 241; (E, I and M) 60-day antibiotic therapy+ID93/GLA-SE, day 295. Data shown are representative of 5 mice/group Whereas 40% of the animals receiving 90 days of chemotherapy alone (Rx90d; -▲-) survived Mtb infection (MST 214 days), 100% of the animals receiving vaccine immunotherapy after 60 days of chemotherapy (-●-) survived for at least 250 days (P<0.05) (FIG. 3A). These studies demonstrate that vaccine immunotherapy could reduce the duration of drug therapy by at least ⅓ while preventing death for an extended period after chemotherapy was withdrawn.

In order to determine if antibiotics combined with ID93/GLA-SE reduced TB lung pathology, sections from mock-, Rx-, and Rx+ID93/GLA-SE-treated mice were taken for histological analysis (Histologic Findings are presented in Table 1 (below) and FIG. 3B-M.

TABLE 1

Effects of ID93/GLA-SE immunotherapy on lung pathology of Mtb-infected SWR/J

| Group[a] | Lesion Grade | Lung (%)[b] | Lung AFB[c] | Granuloma | Diagnosis |
|---|---|---|---|---|---|
| Mock (Day 106) | 3-4 Moderate-marked | 40-100 | 6-30 | Coalescing macrophage nodules, with syncytial giant cells | Histiocytic alveolar and interstitial pneumonia, moderate to marked; granulomatous lobar bronchopneumonia. Numerous AFB in lesions |
| Rx[d] (Day 106) | 0-2 Mild-Moderate | 0-40% | <1 | No nodular granulomas. Few macrophages Resolution of large lesions | Histiocytic alveolar and interstitial pneumonia, mild to moderate. Minimal AFB in lesions |
| Rx[d] (Day 241, 295) | 4 Marked | 41-100 | ≤30 | No significant histiocytic granulomas, no syncytial macrophages | Histiocytic alveolar and interstitial pneumonia, marked. Many AFB in lesions |
| Rx + ID93/GLA-SE[f] (Day 241) | 2 Mild-Moderate | 11-40 | ≤6 | Histiocytic granulomas with syncytial macrophages Several small dense lymphoid aggregates | Histiocytic alveolar and interstitial pneumonia, mild-moderate. Few or no AFB in lesions |
| Rx[e] + ID93/GLA-SE[f] (Day 295) | 1-3 Minimal-Moderate | 0-40 | ≤1-6 | Histiocytic granulomas with syncytial macrophages Minimal, multifocal, infiltration of lymphocytes | Histiocytic alveolar and interstitial pneumonia, minimal-moderate. Few AFB in lesions |

[a]Data are representative of 3-5 animals per group
[b]Percent of lung tissue involved: Minimal (grade 1 or <10%); Mild (grade 2 or 11-20%); Moderate (grade 3 or 21-40%); Marked (grade 4 or 41-100%)
[c]Number of Acid Fast Bacteria (AFB)/High Power Field (HPF), 600x
[d]90 day INH/RIF chemotherapy initiated 15 days following infection with Mtb
[e]60 day INH/RIF chemotherapy initiated 15 days following infection with Mtb
[f]Mice were immunized 3 times, 3 weeks apart after the administration of chemotherapy treatment.

Figure 3J:
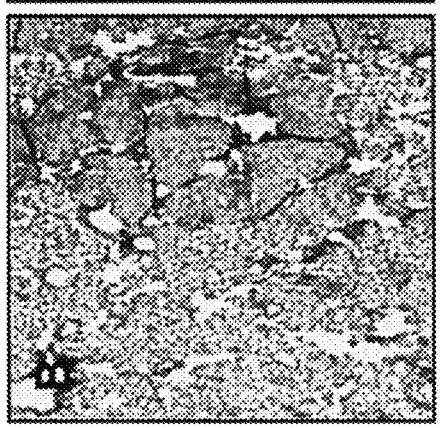
Figure 3C:
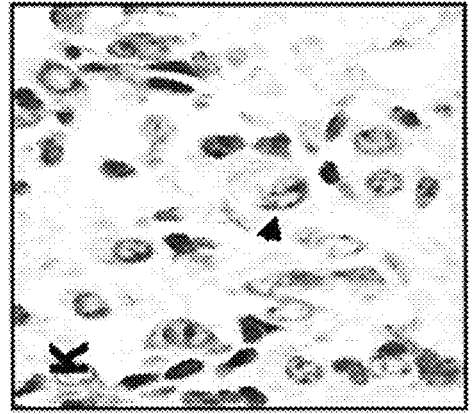
Figure 3G:
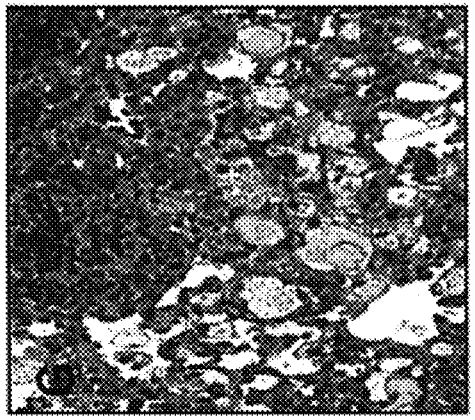
Figure 3K:

The lungs of mock-treated mice had diffuse alveolar edema (FIGS. 3B,F) with grade 3-4 (40-100%) involvement of the lung parenchyma appearing greatly inflamed and necrotic as previously reported [29, 38], with numerous acid-fast bacilli (>30/600×high power field (HPF) (FIG. 3J). The lung sections of the chemotherapy alone (Rx90d) group showed obvious resolution of inflammatory lesions (FIG. 3 C,G) with only rare bacilli (<1/HPF) (FIG. 3 K; Table 1). At day 241, the lungs of Rx 90d-i-ID93/GLA-SE mice had numerous granulomas (Figs. D, H) and few bacilli (<6 organisms/HPF, 600×) (FIG. 3 L; Table 1). At day 295, lungs of mice treated with 60d antibiotics and immunized with ID93/GLA-SE showed no significant lesions (FIGS. 3 E, I; Table 1) and few bacilli (FIG. 3 M).

The data demonstrates that the ID93/GLA-SE vaccine administered in conjunction with antibiotics could be used to shorten standard chemotherapy regimens in active TB infections (FIG. 3A).

Example 4

Immune Responses in SWR/J Mice Receiving Chemotherapy Alone or Chemotherapy Plus SE ID93/GLA-Vaccination Cytokine Profile of ID93-Stimulated Splenocytes SWR/J mice were infected with a LDA Mtb H37Rv and treated with either 90 days of antibiotics alone or antibiotics followed by three immunizations with ID93/GLA-SE 3 weeks apart as described in Example 2. Cytokine profiles from supernatants of ID93-stimulated splenocytes (day 177 or 241 post-infection) were analyzed after incubation for 24 hours in the presence of antigen or media alone by multiplex bead array for IFN-γ, IL-2, TNF, IL-5, IL-10, IL-13, and IL-17. Box plots show median and interquartile range after background subtraction. P-values from Wilcoxon rank sums test.

Intracellular Cytokine Staining for ID93-Specific T-Cell Responses at Days 149 and 177 Postinfection.

Figure 4A:
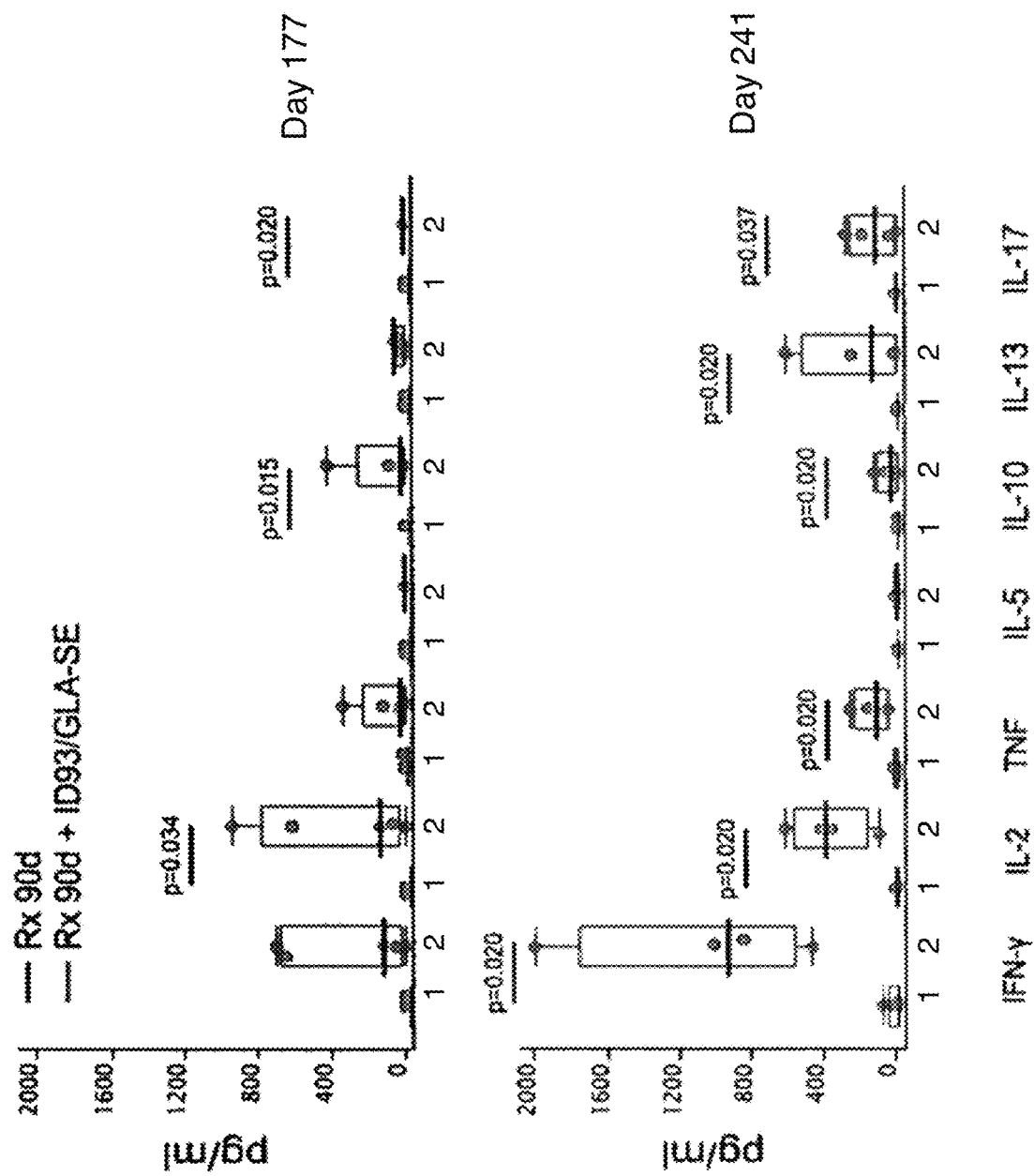

Cells were stimulated with ID93 or media control in the presence of brefeldin A for 8-12 hours, stained with fluorochrome-conjugated antibodies against CD3, CD4, CD8, CD44, IFN-γ, IL-2 and TNF and analyzed by FACS. (B and C) The panels show the gating scheme for FACS analysis. (D) Box plots in lower panel show median and interquartile range after background subtraction. P-values from Wilcoxon rank sums test. In response to in vitro restimulation with ID93, a subset of cytokines representing pro-inflammatory, as well as TH1 and TH2 functional groups, was significantly up-regulated (FIG. 4A). TNF, a soluble mediator of Mtb-specific immunity in infected individuals, was significantly up-regulated at day 241 in the group immunized with ID93/GLA-SE (P<0.05). In addition, ID93-specific IFN-γ, IL-2, and IL-17 responses were detected, which were significantly higher in vaccinated animals compared to unvaccinated animals. No significant difference in the concentration of the TH2-type IL-5 cytokine was detected but significant ID93-specific IL-10 and IL-13 responses were measured at day 241.

Figure 4B:
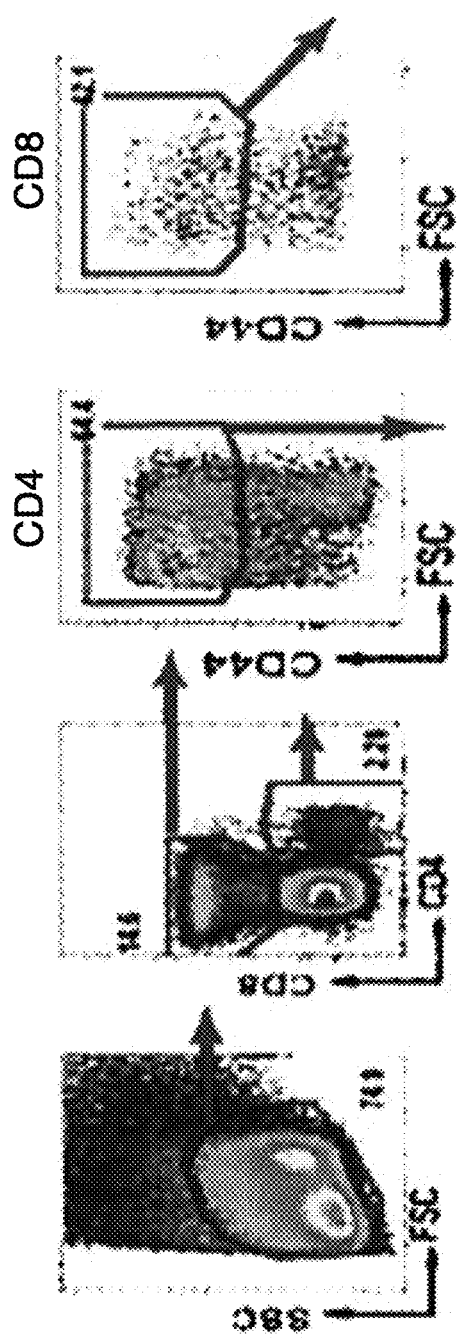
Figure 4C:
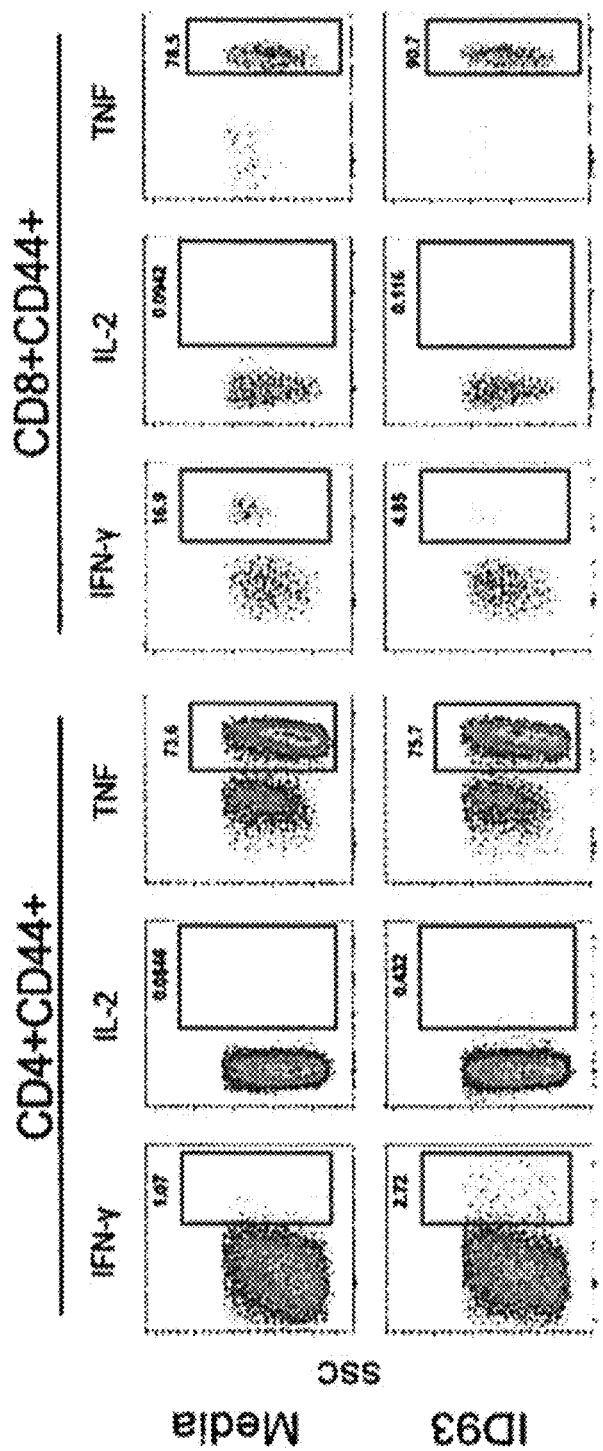
Figure 4D:
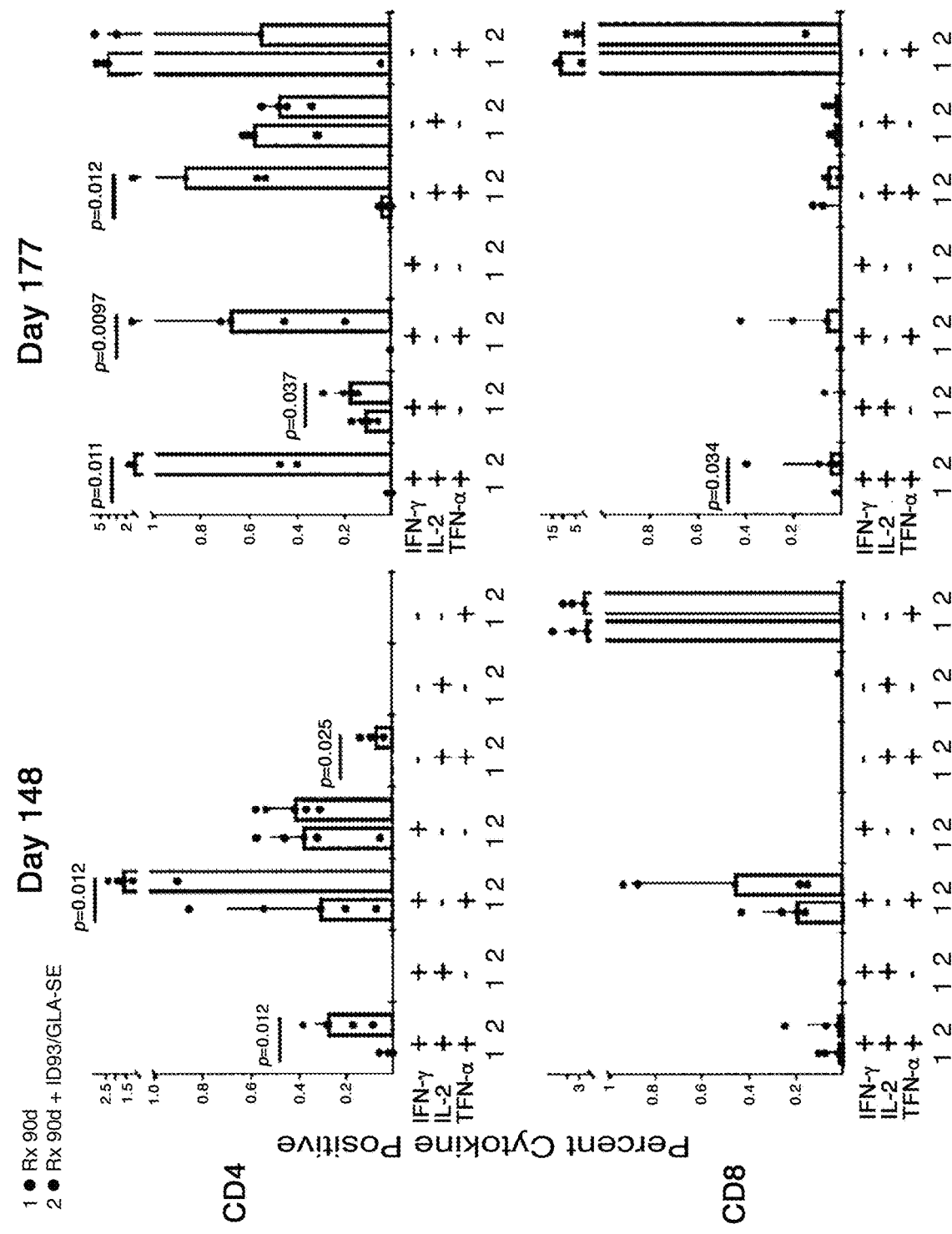

Polyfunctional CD4+ TH1 cells have recently been described as a correlate of protection against *Leishmania major*, and have been implicated in limiting disease progression in human TB [39, 40], Frequencies of CD4+ and CD8+ T cells producing IFN-γ, IL-2 and TNF were thus examined to determine the phenotype of ID93– specific T-cell responses (FIG. 4B-D; S2B). Higher frequencies of ID93-specific polyfunctional triplepositive and IFN-γ+TNF+double-positive CD4+ T cells were observed in mice receiving adjunctive immunotherapy compared to mice receiving only chemotherapy (P<0.05), (FIG. 4B-D). High background responses of ID93– specific TNF in both the CD4+ and CD8+ Tcell subsets were observed which was likely due to the increased immune activation of an ongoing Mtb infection in these animals. Although ID93– specific responses in CD8+ T cells were lower in magnitude than those observed in the CD4+compartment, there were significantly higher frequencies of double (IFN-γ+ TNF+) and triple positive (IFN-γ+IL-2+ TNF+) CD8+ T cells in mice receiving adjunctive ID93/GLA-SE vaccination. Altogether, these data show that though there are many antigens present after Mtb infection that could be potentially primed and boosted continuously, ID93/GLA-SE administered adjunctively with antibiotics was successful at stimulating a significantly more robust, high-quality (polyfunctional) and durable TH 1-type anti-ID93 CD4+ T-cell response.

Example 5

ID93/GLA-SE as an Adjunct to Antibiotic Treatment in Cynomolgus Macaques

Figure 5E:
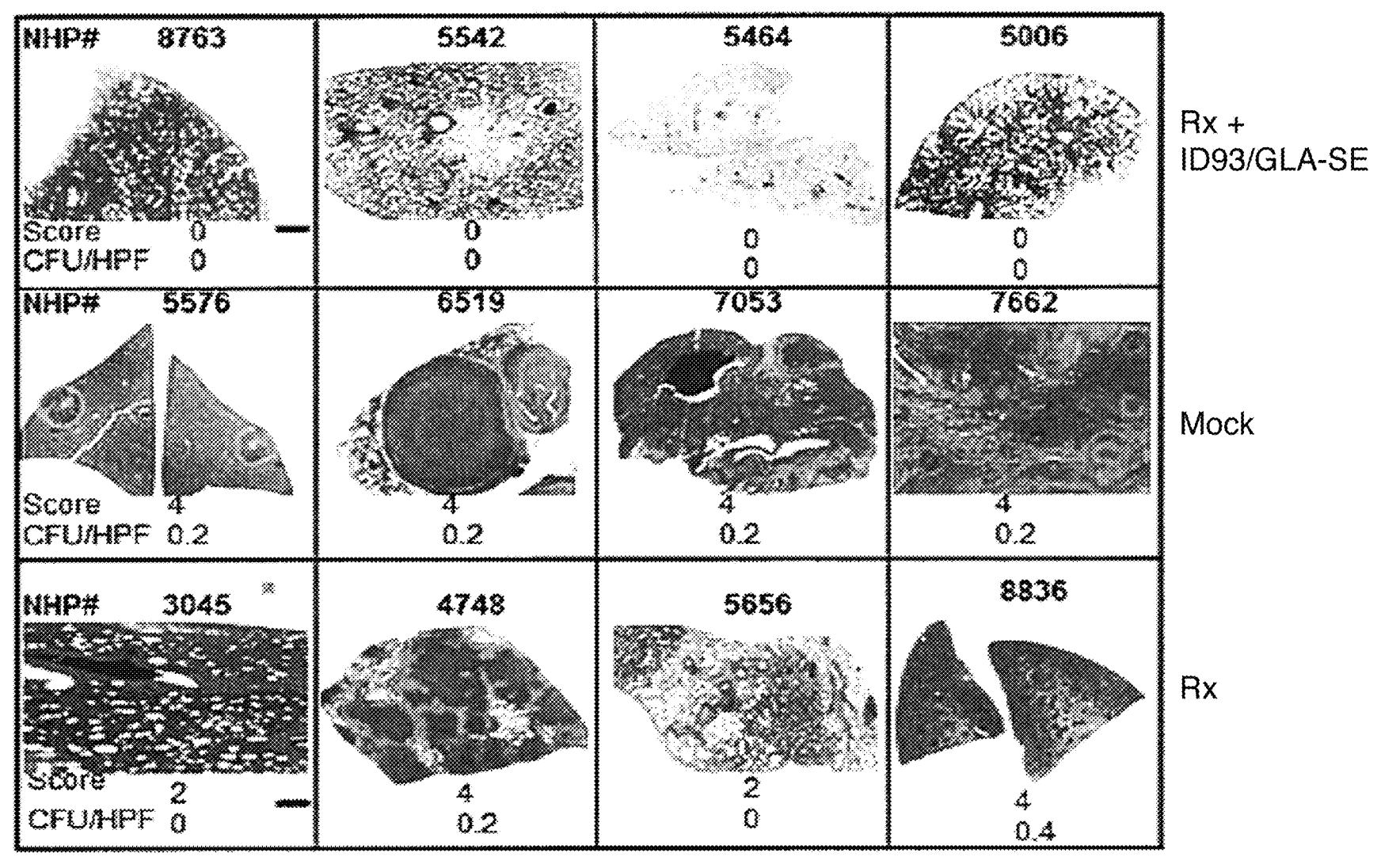

In order to demonstrate the safety of ID93/GLA-SE when administered as an adjunct to antibiotics in NHP, macaques were administered three doses of the vaccine after one month of RIF/INH antibiotics (FIG. 5A). Injection-site reactions were minimal, with no more than barely perceptible erythema and edema (Draize scale range 0-1), and there were no significant changes in body weight and temperature (data not shown). All 7 (100%) of the Rx+ID93/GEA-SE immunized NHP survived to the last time point evaluated, whereas 6 NHP (85.7%) in the antibiotics alone group and 3 NHP (42.8%, P=0.44) in the mock treated group survived to this point (FIG. 5B). Four monkeys treated with Rx+ID93/GEA-SE either had no radiological changes or resolved the Mtb infection before the end of the experiment (as evidenced by lung infiltrates on previously positive chest X-rays), whereas none of the macaques receiving Rx alone or mock treatments resolved their Mtb infection and remained chest X-ray positive (FIG. 5C). Forty percent of the macaques treated with Rx+ID93/GEA-SE responded dramatically to adjunctive immunotherapy by showing quantitative differences in Mtb bacterial numbers when compared to the Rx alone group; (P<0.05) (FIG. 5D). Interestingly, the Rx+ID93/GEA-SE macaques that had lower CFU counts also had negative chest X-rays at the end of the experiment. There was also a correlation by histopathology between group assignment and the presence of disease tissue, with animals receiving ID93/GEA-SE containing the most healthy organs and the saline group having the most diseased organs (p=0.003) (FIG. 5E). Overall, these results demonstrated that an ID93/GEASE vaccine was well tolerated as a post exposure immunotherapeutic agent in cynomolgus macaques.

Example 6

Immune Responses in BALB/c Mice Receiving Chemotherapy Alone or Chemotherapy Plus ID83/GLA-SE Vaccination Six-week-old female BAEB/c mice (Charles River, Wilmington, Mass.) were infected with *M. tuberculosis* H37Rv, using the Inhalation Exposure System (Glas-Col, Terne Haute, IN) and a log phase broth culture (optical density at 600 nm of 1.0) diluted 10 in 7H9 broth with the goal of implanting 2.5-3.0 $\log_{10}$ CFU in the lungs. *M. tuberculosis* H37Rv was prepared from mouse-passaged, frozen in aliquots, and sub-cultured in Middlebrook 7H9 broth with 10% oleic acid-albumin-dextrose-catalase (OADC) (Fisher, Pittsburgh, Pa.) and 0.05% Tween 80 prior to infection. Five mice were sacrificed 1 day after infection to confirm the number of bacteria implanted. The remaining mice were randomized to the treatment groups indicated in Table 2. Treatment with rifampin (R), isoniazid (H) and pyrazinamide (Z) collectively RHZ started 26 days after infection on Day 0. Rifampin and isoniazid (Sigma, St. Louis, Mo.) were dissolved separately in distilled water at 1 mg/ml to produce the dosing solution. Pyrazinamide (Fisher Scientific, Suwanee, Ga.) was dissolved in distilled water at 15 mg/ml to produce the dosing solution. Solutions were prepared and aliquotted weekly and kept at 4° C. prior to use. Four control groups received drug vehicle (water)+GLA-SE adjuvant, drug vehicle+ID83 vaccine, RHZ+vaccine vehicle (saline), and RHZ+GLA-SE adjuvant. The test group received RHZ+ID83 vaccine. RHZ and drug vehicle were administered 5 days per week, by gavage, for 12 weeks. R or vehicle was administered at least 1 hour before HZ or vehicle to avoid previously described pharmacokinetic drug-drug interactions which limit R absorption.

ID83 was formulated as a stable oil-in-water emulsion adjuvanted with GLA (GLASE) by mixing 4 ml of vaccine mixture were prepared with 2 ml GLA-SE (0.040 mg/ml, 4% Oil), 0.1 ml ID83 (0.2 mg/ml) and 1.9 ml saline (NaCl). The vaccine preparation was vortexed briefly before use. 100 μl of vaccine was administered subcutaneously. The injected doses were: 2 μg of GLA-SE+/−0.5 μg of ID83.

Vaccination of infected mice began 6 weeks after infection (2 weeks after treatment RHZ initiation). Three doses of vaccine or controls (saline or adjuvant only) were administered subcutaneously in 100 microliters at 3 week intervals (i.e., after 2, 5 and 8 weeks of treatment). The vaccine contained 2 micrograms of GLA-SE adjuvant and 0.5 micrograms of ID83. Controls included saline only and adjuvant only. The site of injection was rotated.

TABLE 2

Experimental scheme

| Regimen* | No. mice to sacrifice by time-point | | | | | Total |
|---|---|---|---|---|---|---|
| | Wk −4 | Day 0 | Wk 6 | Wk 12 | Wk 12 + 5** | Wk 12 + 10** | |
| Vehicle + Adjuvant | 5 | 5 | 5 | 5 | | | 20 |
| Vehicle + Vaccine | | | 5 | 5 | | | 10 |
| RHZ + Saline | | | 5 | 5 | 5 | 5 | 20 |
| RHZ + Adjuvant | | | 5 | 5 | 5 | 5 | 20 |
| RHZ + Vaccine | | | 5 | 5 | 5 | 5 | 20 |
| Total | 5 | 5 | 25 | 25 | 15 | 15 | 90 |

*Vehicle is water; Adjuvant is GLA-SE; Vaccine is ID83 + GLA-SE
**Wks 12 + 5 and 12 + 10 indicate the time point following 12 weeks of treatment, plus 5 and 10 weeks of follow-up without any treatment.

Pathological Assessment.

Photographs of representative lungs were taken after 72 hours of incubation in sterile PBS, and before homogenization for quantitative cultures, to record the macroscopic appearance of lung lesions. The other lung was washed and placed in 10% neutral-buffered formalin solution. These lungs were embedded in paraffin, sectioned, fixed on glass slides and stained with H&E and an acid-fast stain for review of histopathology.

Histopathology Assessment.

CFU counts (x) were log-transformed as (x+1) before analysis. Group means were compared by one-way analysis of variance with Bonferroni's post-test.

Results

Lung CFU Counts During Treatment.

Figure 6A:
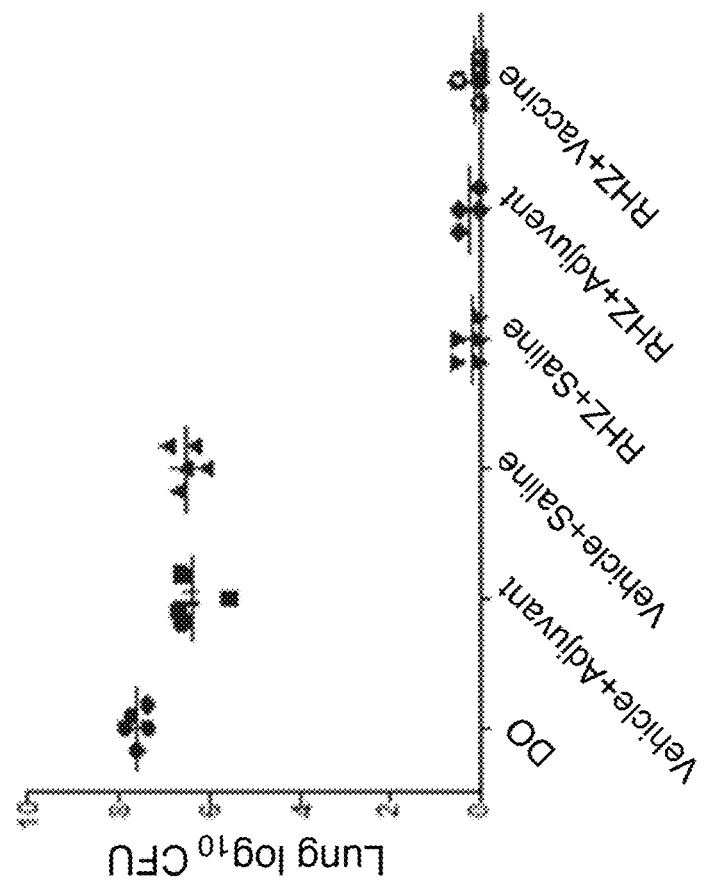
FIGS. 6A and 6B shows lung $\log_{10}$ CFU counts after 6 weeks of treatment (FIG. 6A) and after 12 weeks of treatment (FIG. 6B).
Figure 6B:
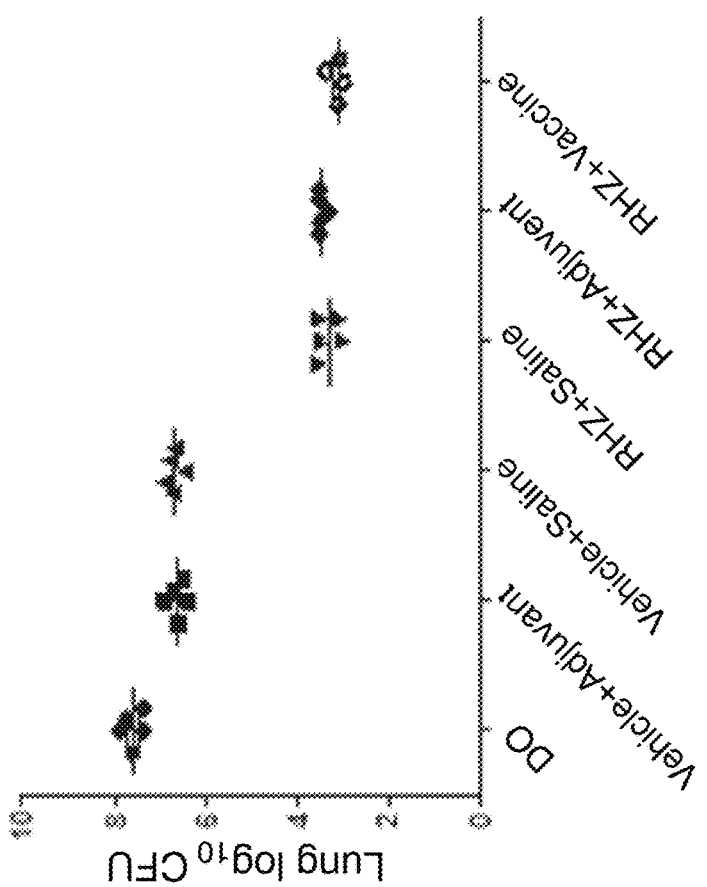

The mean (+SD) lung $\log_{10}$ CFU count at D-26 was 2.78+0.21. The mean CFU count at the staid of treatment (DO) was 7.60+0.23. After 6 weeks of treatment, lung CFU counts declined by approximately 0.9 $\log_{10}$ in the vehicle+adjuvant and vehicle+vaccine groups, whereas the CFU counts in the RHZ+saline, RHZ+adjuvant and RHZ+vaccine groups fell by 4.27, 4.19 and 4.44 $\log_{10}$, respectively (FIG. 6A). After 12 weeks of treatment, the CFU counts in the drug vehicle-treated groups were largely stable, whereas 3 of 5, 2 of 4, and 4 of 5 mice treated with antibiotics alone (RHZ+saline), antibiotic plus TLR4 adjuvant (RHZ+adjuvant), and antibiotics+ID 83 vaccine (RHZ+Vaccine), respectively, were culture-negative (FIG. 6).

Lung CFU Counts after Treatment Completion.

Figure 7:
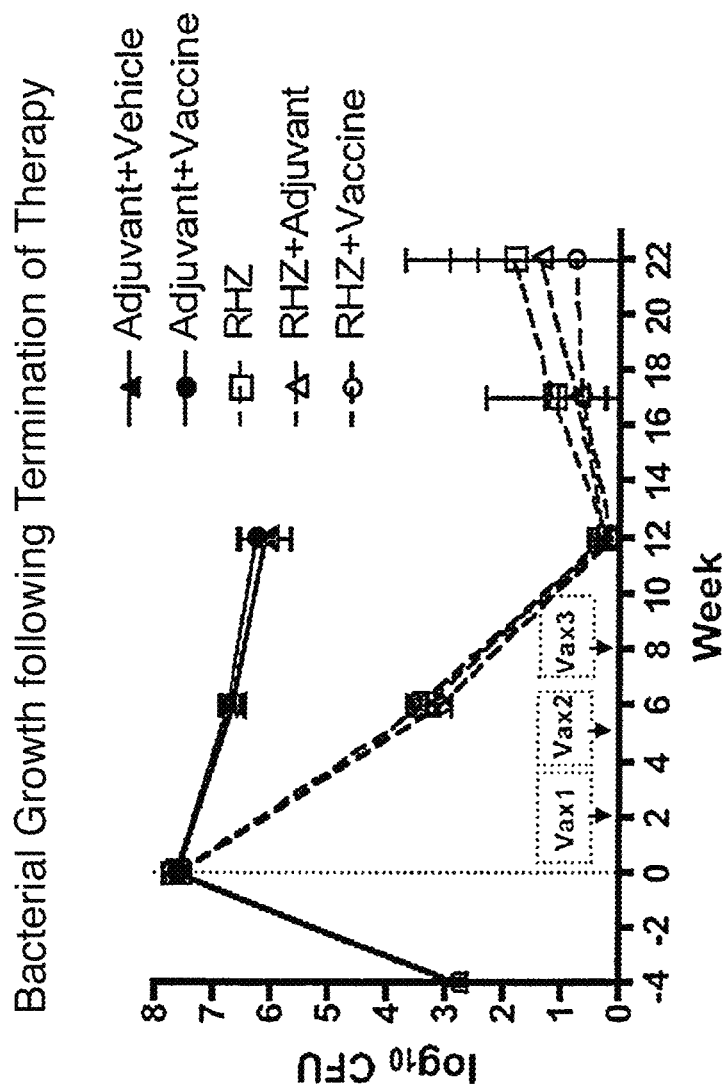
FIG. 7 shows bacterial growth following termination of therapy.

After 5 weeks of followup post cessation of any treatment, 4 of 5 mice in each group had positive lung cultures (Table 3 below). The mean lung $\log_{10}$ CFU counts in RHZ+saline, RHZ+adjuvant and RHZ+vaccine groups were 1.14+1.14, 0.72+0.49 and 0.63+0.42, respectively. Excluding the culture negative mice, the CFU counts were 1.42+1.09, 0.90+0.32, and 0.78+0.27, respectively. After 10 weeks of follow-up, only 1 of 5 mice in the RHZ+vaccine group had a positive culture, compared to 3 of 5 mice in the RHZ+adjuvant and RHZ+saline groups. Excluding the culture-negative mice, the mean $\text{lung}_{10}$ CFU counts in RHZ+saline, RHZ+adjuvant and RHZ+vaccine groups were 1.82+1.85, 1.37+1.56 and 0.75+1.68, respectively. At ten weeks after termination of treatment (FIG. 7), the CFU counts in the three animals with positive lung cultures in both groups treated with RHZ+saline or RHZ+adjuvant alone exhibited logarithmic bacterial regrowth, while the only animal with positive lung culture in the RHZ+vaccine group exhibited bacterial regrowth that was reduced compared to the other two groups.

While the study was not powered for statistical significance in terms of CFU counts, these data demonstrated that treatment of an active tuberculosis according to the methods of the invention results in a durable improvement in a sign or symptom of tuberculosis and provide for a shortening of the duration of chemotherapy compared antibiotic drug therapy alone.

TABLE 3

Percentage (proportion) of mice with positive cultures after 12 weeks of treatment followed by 5 or 10 weeks of follow-up

| | Follow-up time point | |
|---|---|---|
| Regimen | Wk 12 + 5 | Wk 12 + 10 |
| RHZ + Saline | 80% (4/5) | 60% (3/5) |
| RHZ + Adjuvant | 80% (4/5) | 60% (3/5) |
| RHZ + Vaccine | 80% (4/5) | 20% (1/5) |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

Exemplar Amino Acid Sequences

```
ID93 fusion polypeptide with optional His tag
                                       (SEQ ID NO: 1)
MGSSHHHHHHSSGLVPRGSHMTINYQFGDVDAHGAMIRAQAGSLEAEHQAI
```

-continued

ISDVLTASDFWGGAGSAACQGFITQLGRNFQVIYEQANAHGQKVQAAGNNM

AQTDSAVGSSWAGTHLANGSMSEVMMSEIAGLPIPPIIHYGAIAYAPSGAS

GKAWHQRTPARAEQVALEKCGDKTCKVVSRFTRCGAVAYNGSKYQGGTGLT

RRAAEDDAVNRLEGGRIVNWACNELMTSRFMTDPHAMRDMAGRFEVHAQTV

EDEARRMWASAQNISGAGWSGMAEATSLDTMTQMNQAFRNIVNMLHGVRDG

LVRDANNYEQQEQASQQILSSVDINFAVLPPEVNSARIFAGAGLPMLAAA

SAWDGLAEELHAAAGSFASVTTGLAGDAWHGPASLAMTRAASPYVGWLNTA

AGQAAQAAGQARLAASAFEATLAATVSPAMVAANRTRLASLVAANLLGQNA

PAIAAAEAEYEQIWAQDVAAMFGYHSAASAVATQLAPIQEGLQQQLQNVLA

QLASGNLGSGNVGVGNIGNDNIGNANIGFGNRGDANIGIGNIGDRNLGIGN

TGNWNIGIGITGNGQIGFGKPANPDVLVVGNGGPGVTALVMGGTDSLLPLP

NIPLLEYAARFITPVHPGYTATFLETPSQFFPFTGLNSLTYDVSVAQGVTN

LHTAIMAQLAAGNEVVVFGTSQSATIATFEMRYLQSLPAHLRPGLDELSFT

LTGNPNRPDGGILTRFGFSIPQLGFTLSGATPADAYPTVDYAFQYDGVNDF

PKYPLNVFATANAIAGILFLHSGLIALPPDLASGVVQPVSSPDVLTTYILL

PSQDLPLLVPLRAIPLLGNPLADLIQPDLRVLVELGYDRTAHQDVPSPFGL

FPDVDWAEVAADLQQGAVQGVNDALSGLGLPPPWQPALPRLFST

ID93 fusion polypeptide
(SEQ ID NO: 2)
MTINYQFGDVDAHGAMIRAQAGSLEAEHQAIISDVLTASDFWGGAGSAACQ

GFITQLGRNFQVIYEQANAHGQKVQAAGNNMAQTDSAVGSSWAGTHLANGS

MSEVMMSEIAGLPIPPIIHYGAIAYAPSGASGKAWHQRTPARAEQVALEKC

GDKTCKVVSRFTRCGAVAYNGSKYQGGTGLTRRAAEDDAVNRLEGGRIVNW

ACNELMTSRFMTDPHAMRDMAGRFEVHAQTVEDEARRMWASAQNISGAGWS

GMAEATSLDTMTQMNQAFRNIVNMLHGVRDGLVRDANNYEQQEQASQQILS

SVDINFAVLPPEVNSARIFAGAGLPMLAAASAWDGLAEELHAAAGSFASV

TTGLAGDAWHGPASLAMTRAASPYVGWLNTAAGQAAQAAGQARLAASAFEA

TLAATVSPAMVAANRTRLASLVAANLLGQNAPAIAAAEAEYEQIWAQDVAA

MFGYHSAASAVATQLAPIQEGLQQQLQNVLAQLASGNLGSGNVGVGNIGND

NIGNANIGFGNRGDANIGIGNIGDRNLGIGNTGNWNIGIGITGNGQIGFGK

PANPDVLVVGNGGPGVTALVMGGTDSLLPLPNIPLLEYAARFITPVHPGYT

ATFLETPSQFFPFTGLNSLTYDVSVAQGVTNLHTA1MAQLAAGNEVVVFGT

SQSATIATFEMRYLQSLPAHLRPGLDELSFTLTGNPNRPDGGILTRFGFSI

PQLGFTLSGATPADAYPTVDYAFQYDGVNDFPKYPLNVFATANAIAGILFL

HSGLIALPPDLASGVVQPVSSPDVLTTYILLPSQDLPLLVPLRAIPLLGNP

LADLIQPDLRVLVELGYDRTAHQDVPSPFGLFPDVDWAEVAADLQQGAVQG

VNDALSGLGLPPPWQPALPRLFST

ID83 fusion polypeptide with optional His tag
(SEQ ID NO: 3)
MGSSHHHHHHSSGLVPRGSHMGTHLANGSMSEVMMSEIAGLPIPPIIHYGA

IAYAPSGASGKAWHQRTPARAEQVALEKCGDKTCKVVSRFTRCGAVAYNGS

KYQGGTGLTRRAAEDDAVNRLEGGRIVNWACNELMTSRFMTDPHAMRDMAG

-continued

RFEVHAQTVEDEARRMWASAQNISGAGWSGMAEATSLDTMTQMNQAFRNIV

NMLHGVRDGLVRDANNYEQQEQASQQILSSVDINFAVLPPEVNSARIFAGA

GLGPMLAAASAWDGLAEELHAAAGSFASVTTGLAGDAWHGPASLAMTRAAS

PYVGWLNTAAGQAAQAAGQARLAASAFEATLAATVSPAMVAANRTRLASLV

AANLLGQNAPAIAAAEAEYEQIWAQDVAAMFGYHSAASAVATQLAPIQEGL

QQQLQNVLAQLASGNLGSGNVGVGNIGNDNIGNANIGFGNRGDANIGIGNI

GDRNLGIGNTGNWNIGIGITGNGQIGFGKPANPDVLVVGNGGPGVTALVMG

GTDSLLPLPNIPLLEYAARFITPVHPGYTATFLETPSQFFPFTGLNSLTYD

VSVAQGVTNLHTAIMAQLAAGNEVVVFGTSQSATIATFEMRYLQSLPAHLR

PGLDELSFTLTGNPNRPDGGILTRFGFSIPQLGFTLSGATPADAYPTVDYA

FQYDGVNDFPKYPLNVFATANAIAGILFLHSGLIALPPDLASGVVQPVSSP

DVLTTYILLPSQDLPLLVPLRAIPLLGNPLADLIQPDLRVLVELGYDRTAH

QDVPSPFGLFPDVDWAEVAADLQQGAVQGVNDALSGLGLPPPWQPALPRLF

ST

ID83 fusion polypeptide
(SEQ ID NO: 4)
HLANGSMSEVMMSEIAGLPIPPI1HYGAIAYAPSGASGKAWHQRTPARAEQ

VALEKCGDKTCKVVSRFTRCGAVAYNGSKYQGGTGLTRRAAEDDAVNRLEG

GRIVNWACNELMTSRFMTDPHAMRDMAGRFEVHAQTVEDEARRMWASAQNI

SGAGWSGMAEATSLDTMTQMNQAFRNIVNMLHGVRDGLVRDANNYEQQEQA

SQQILSSVDINFAVLPPEVNSARIFAGAGLPMLAAASAWDGLAEELHAAA

GSFASVTTGLAGDAWHGPASLAMTRAASPYVGWLNTAAGQAAQAAGQARLA

ASAFEATLAATVSPAMVAANRTRLASLVAANLLGQNAPAIAAAEAEYEQIW

AQDVAAMFGYHSAASAVATQLAPIQEGLQQQLQNVLAQLASGNLGSGNVGV

GNIGNDNIGNANIGFGNRGDANIGIGNIGDRNLGIGNTGNWNIGIGITGNG

QIGFGKPANPDVLVVGNGGPGVTALVMGGTDSLLPLPNIPLLEYAARFITP

VHPGYTATFLETPSQFFPFTGLNSLTYDVSVAQGVTNLHTAIMAQLAAGNE

VVVFGTSQSATIATFEMRYLQSLPAHLRPGLDELSFTLTGNPNRPDGGILT

RFGFSIPQLGFTLSGATPADAYPTVDYAFQYDGVNDFPKYPLNVFATANAI

AGILFLHSGLIALPPDLASGVVQPVSSPDVLTTYILLPSQDLPLLVPLRAI

PLLGNPLADLIQPDLRVLVELGYDRTAHQDVPSPFGLFPDVDWAEVAADLQ

QGAVQGVNDALSGLGLPPPWQPALPRLFST

Rv1813
(SEQ ID NO: 5)
MITNLRRRTAMAAAGLGAALGLGILLVPTVDAHLANGSMSEVMMSEIAGLP

IPPIIHYGALAYAPSGASGKAWHQRTPARAEQVALEKCGDKTCKVVSRFTR

CGAVAYNGSKYQGGTGLTRRAAEDDAVNRLEGGRIVNWACN

Rv3620
(SEQ ID NO: 6)
MTSRFMTDPHAMRDMAGRFEVHAQTVEDEARRMWASAQNISGAGWSGMAEA

TSLDTMTQMNQAFRNIVNMLHGVRDGLVRDANNYEQQEQASQQILSS

Rv2608
(SEQ ID NO: 7)
MNFAVLPPEVNSARIFAGAGLPMLAAASAWDGLAEELHAAAGSFASVTTG

LAGDAWHGPASLAMTRAASPYVGWLNTAAGQAAQAAGQARLAASAFEATLA

ATVSPAMVAANRTRLASLVAANLLGQNAPAIAAAEAEYEQIWAQDVAAMFG

YHSAASAVATQLAPIQEGLQQQLQNVLAQLASGNLGSGNVGVGNIGNDNIG

NANIGFGNRGDANIGIGNIGDRNLGIGNTGNWNIGIGITGNGQIGFGKPAN

PDVLVVGNGGPGVTALVMGGTDSLLPLPNIPLLEYAARFITPVHPGYTATF

LETPSQFFPFTGLNSLTYDVSVAQGVTNLHTAIMAQLAAGNEVVVFGTSQS

ATIATFEMRYLQSLPAHLRPGLDELSFTLTGNPNRPDGGILTRFGFSIPQL

GFTLSGATPADAYPTVDYAFQYDGVNDFPKYPLNVFATANAIAGILFLHSG

LIALPPDLASGVVQPVSSPDVLTTYILLPSQDLPLLVPLRAIPLLGNPLAD

LIQPDLRVLVELGYDRTAHQDVPSPFGLFPDVDWAEVAADLQQGAVQGVND

ALSGLGLPPPWQPALPRLF

Rv3619
(SEQ ID NO: 8)

MTINYQFGDVDAHGAMIRAQAGSLEAEHQAIISDVLTASDFWGGAGSAACQ

GFITQLGRNFQVIYEQANAHGQKVQAAGNNMAQTDSAVGSSWA

What is claimed is:

1. A method for treating an active tuberculosis infection in a human, the method comprising the step of administering to a human having an active tuberculosis infection an immunologically effective amount of a therapeutic vaccine in conjunction with one or more chemotherapeutic agents, wherein the vaccine comprises a pharmaceutical composition comprising an isolated fusion polypeptide, wherein the fusion polypeptide comprises (a) a combination of the Rv1813, Rv3620, and Rv2608 antigens from a *Mycobacterium* species of a tuberculosis complex and the antigens are covalently linked, or (b) a sequence having at least 90% identity to the sequence of the fusion polypeptide; and wherein the active tuberculosis infection is characterized by *Mycobacterium tuberculosis* bacteria that proliferate, reproduce, expand, or actively multiply at an exponential, logarithmic, or semilogarithmic rate in an organ of the human or wherein the active tuberculosis infection is associated with a clinical symptom.

2. The method of claim 1, wherein the therapeutic vaccine comprises a fusion polypeptide comprising (a) a combination of *Mycobacterium* antigen Rv2608, Rv3619, Rv3620, and Rv1813, or (b) a sequence having at least 90% sequence identity to the sequence of the fusion polypeptide.

3. The method of claim 2, wherein the *Mycobacterium* antigens Rv2608, Rv3619, Rv3620 and Rv1813 are *M. tuberculosis* antigens Rv2608, Rv3619, Rv3620 and Rv1813.

4. The method of claim 1, wherein the fusion polypeptide comprises the amino acid sequence set forth in SEQ ID NO:1, or a sequence having at least 90% identity thereto.

5. A method for treating an active tuberculosis infection in a human, the method comprising the step of administering to a human having an active tuberculosis infection an immunologically effective amount of a therapeutic vaccine in conjunction with one or more chemotherapeutic agents, wherein the vaccine comprises a pharmaceutical composition comprising an isolated fusion polypeptide, wherein the fusion polypeptide comprises the amino acid sequence set forth in SEQ ID NO:2, or a sequence having at least 90% identity thereto, and wherein the active tuberculosis infection is characterized by *Mycobacterium tuberculosis* bacteria that proliferate, reproduce, expand, or actively multiply at an exponential, logarithmic, or semilogarithmic rate in an organ of the human or wherein the active tuberculosis infection is associated with a clinical symptom.

6. The method of claim 1, wherein the combination of *Mycobacterium* antigen consists of Rv2608, Rv3620 and Rv1813.

7. The method of claim 6, wherein the *Mycobacterium* antigens Rv2608, Rv3620 and Rv1813 are *M. tuberculosis* antigens Rv2608, Rv3620 and Rv1813.

8. The method of claim 1, wherein the fusion polypeptide comprises the amino acid sequence set forth in SEQ ID NO:3 or SEQ ID NO:4, or a sequence having at least 90% identity to SEQ ID NO:3 or SEQ ID NO:4.

9. The method of claim 1, wherein the active tuberculosis infection is an active primary infection of *M. tuberculosis*.

10. The method of claim 1, wherein the active tuberculosis infection is a reactivation tuberculosis infection.

11. The method of claim 1, wherein the human is infected with a multidrug resistant (MDR) *M. tuberculosis*.

12. The method of claim 1, wherein the human was previously immunized with *Bacillus* Calmette-Guerin (BCG).

13. The method of claim 1, wherein the one or more chemotherapeutic agents is isoniazid, rifampin, amikacin, aminosalicylic acid, capreomycin, cycloserine, ethambutol, ethionamide, kanamycin, pyrazinamide, rifapentine, rifabutin, streptomycin, ofloxacin, ciprofloxacin, clarithromycin, azithromycin, fluoroquinolones, or a combination thereof.

14. The method of claim 1, wherein the human is first administered one or more chemotherapeutic agents over a period of time and subsequently administered the therapeutic vaccine.

15. The method of claim 1, wherein the human is first administered the therapeutic vaccine and subsequently administered one or more chemotherapeutic agents over a period of time.

16. The method of claim 1, wherein administration of the one or more chemotherapeutic agents and the therapeutic vaccine is concurrent.

17. The method of claim 1, further comprising administering the therapeutic vaccine to the human one or more subsequent times, wherein a tuberculosis infection remaining in the human at the one or more subsequent times may or may not be an active tuberculosis infection.

18. The method of claim 1, wherein the vaccine further comprises an adjuvant.

19. The method of claim 18, wherein the adjuvant is GLA, having the following structure:

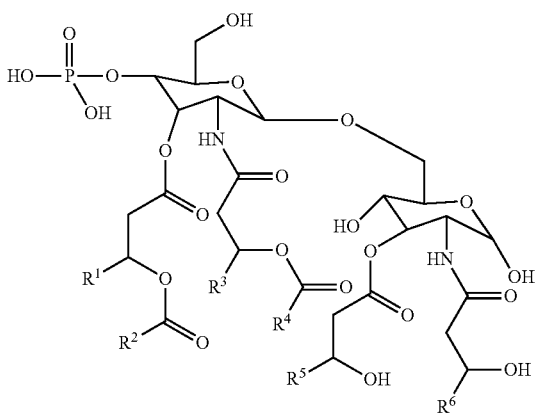

wherein $R^1$, $R^3$, $R^5$, and $R^6$ are $C_{11}$-$C_{20}$ alkyl; and $R^2$ and $R^4$ are $C_9$-$C_{20}$ alkyl.

20. The method of claim 19, wherein $R^1$, $R^3$, $R^5$, and $R^6$ are $C_{11-14}$ alkyl; and $R^2$ and $R^4$ are $C_{12-15}$ alkyl.

21. The method of claim 19, wherein $R^1$, $R^3$, $R^5$ and $R^6$ are $C_{11}$ alkyl; and $R^2$ and $R^4$ are $C_{13}$ alkyl.

22. The method of claim 19, wherein $R^1$, $R^3$, $R^5$ and $R^6$ are $C_{11}$ alkyl; and $R^2$ and $R^4$ are $C_9$ alkyl.

23. The method of claim 1, wherein a N-terminal leader sequence or a transmembrane domain of Rv1813has been removed.

24. The method of claim 2, wherein a N-terminal leader sequence or a transmembrane domain of Rv1813 has been removed.

25. The method of claim 6, wherein a N-terminal leader sequence or a transmembrane domain of Rv1813 has been removed.

* * * * *

SEQUENCE LISTING

<160> NUMBER OF SEQ ID NOS: 8

<210> SEQ ID NO 1
<211> LENGTH: 911
<212> TYPE: PRT
<213> ORGANISM: Artificial Sequence
<220> FEATURE:
<223> OTHER INFORMATION: Synthetic Construct

<400> SEQUENCE: 1

Met Gly Ser Ser His His His His His His Ser Ser Gly Leu Val Pro
1               5                   10                  15

Arg Gly Ser His Met Thr Ile Asn Tyr Gln Phe Gly Asp Val Asp Ala
            20                  25                  30

His Gly Ala Met Ile Arg Ala Gln Ala Gly Ser Leu Glu Ala Glu His
        35                  40                  45

Gln Ala Ile Ile Ser Asp Val Leu Thr Ala Ser Asp Phe Trp Gly Gly
    50                  55                  60

Ala Gly Ser Ala Ala Cys Gln Gly Phe Ile Thr Gln Leu Gly Arg Asn
65                  70                  75                  80

Phe Gln Val Ile Tyr Glu Gln Ala Asn Ala His Gly Gln Lys Val Gln
                85                  90                  95

Ala Ala Gly Asn Asn Met Ala Gln Thr Asp Ser Ala Val Gly Ser Ser
            100                 105                 110

Trp Ala Gly Thr His Leu Ala Asn Gly Ser Met Ser Glu Val Met Met
        115                 120                 125

Ser Glu Ile Ala Gly Leu Pro Ile Pro Ile Ile His Tyr Gly Ala
    130                 135                 140

Ile Ala Tyr Ala Pro Ser Gly Ala Ser Gly Lys Ala Trp His Gln Arg
145                 150                 155                 160

Thr Pro Ala Arg Ala Glu Gln Val Ala Leu Glu Lys Cys Gly Asp Lys
                165                 170                 175

Thr Cys Lys Val Val Ser Arg Phe Thr Arg Cys Gly Ala Val Ala Tyr
            180                 185                 190

Asn Gly Ser Lys Tyr Gln Gly Gly Thr Gly Leu Thr Arg Arg Ala Ala
        195                 200                 205

Glu Asp Asp Ala Val Asn Arg Leu Glu Gly Gly Arg Ile Val Asn Trp
    210                 215                 220

Ala Cys Asn Glu Leu Met Thr Ser Arg Phe Met Thr Asp Pro His Ala
225                 230                 235                 240

Met Arg Asp Met Ala Gly Arg Phe Glu Val His Ala Gln Thr Val Glu
                245                 250                 255

Asp Glu Ala Arg Arg Met Trp Ala Ser Ala Gln Asn Ile Ser Gly Ala
            260                 265                 270

```
Gly Trp Ser Gly Met Ala Glu Ala Thr Ser Leu Asp Thr Met Thr Gln
            275                 280                 285

Met Asn Gln Ala Phe Arg Asn Ile Val Asn Met Leu His Gly Val Arg
    290                 295                 300

Asp Gly Leu Val Arg Asp Ala Asn Asn Tyr Glu Gln Gln Glu Gln Ala
305                 310                 315                 320

Ser Gln Gln Ile Leu Ser Ser Val Asp Ile Asn Phe Ala Val Leu Pro
                325                 330                 335

Pro Glu Val Asn Ser Ala Arg Ile Phe Ala Gly Ala Gly Leu Gly Pro
                340                 345                 350

Met Leu Ala Ala Ala Ser Ala Trp Asp Gly Leu Ala Glu Glu Leu His
            355                 360                 365

Ala Ala Ala Gly Ser Phe Ala Ser Val Thr Thr Gly Leu Ala Gly Asp
        370                 375                 380

Ala Trp His Gly Pro Ala Ser Leu Ala Met Thr Arg Ala Ala Ser Pro
385                 390                 395                 400

Tyr Val Gly Trp Leu Asn Thr Ala Ala Gly Gln Ala Ala Gln Ala Ala
                405                 410                 415

Gly Gln Ala Arg Leu Ala Ala Ser Ala Phe Glu Ala Thr Leu Ala Ala
            420                 425                 430

Thr Val Ser Pro Ala Met Val Ala Ala Asn Arg Thr Arg Leu Ala Ser
        435                 440                 445

Leu Val Ala Ala Asn Leu Leu Gly Gln Asn Ala Pro Ala Ile Ala Ala
    450                 455                 460

Ala Glu Ala Glu Tyr Glu Gln Ile Trp Ala Gln Asp Val Ala Ala Met
465                 470                 475                 480

Phe Gly Tyr His Ser Ala Ala Ser Ala Val Ala Thr Gln Leu Ala Pro
                485                 490                 495

Ile Gln Glu Gly Leu Gln Gln Leu Gln Asn Val Leu Ala Gln Leu
            500                 505                 510

Ala Ser Gly Asn Leu Gly Ser Gly Asn Val Gly Val Gly Asn Ile Gly
        515                 520                 525

Asn Asp Asn Ile Gly Asn Ala Asn Ile Gly Phe Gly Asn Arg Gly Asp
    530                 535                 540

Ala Asn Ile Gly Ile Gly Asn Ile Gly Asp Arg Asn Leu Gly Ile Gly
545                 550                 555                 560

Asn Thr Gly Asn Trp Asn Ile Gly Ile Gly Ile Thr Gly Asn Gly Gln
                565                 570                 575

Ile Gly Phe Gly Lys Pro Ala Asn Pro Asp Val Leu Val Val Gly Asn
            580                 585                 590

Gly Gly Pro Gly Val Thr Ala Leu Val Met Gly Gly Thr Asp Ser Leu
        595                 600                 605

Leu Pro Leu Pro Asn Ile Pro Leu Leu Glu Tyr Ala Ala Arg Phe Ile
    610                 615                 620

Thr Pro Val His Pro Gly Tyr Thr Ala Thr Phe Leu Glu Thr Pro Ser
625                 630                 635                 640

Gln Phe Phe Pro Phe Thr Gly Leu Asn Ser Leu Thr Tyr Asp Val Ser
                645                 650                 655

Val Ala Gln Gly Val Thr Asn Leu His Thr Ala Ile Met Ala Gln Leu
            660                 665                 670

Ala Ala Gly Asn Glu Val Val Phe Gly Thr Ser Gln Ser Ala Thr
        675                 680                 685
```

```
Ile Ala Thr Phe Glu Met Arg Tyr Leu Gln Ser Leu Pro Ala His Leu
690                 695                 700

Arg Pro Gly Leu Asp Glu Leu Ser Phe Thr Leu Thr Gly Asn Pro Asn
705                 710                 715                 720

Arg Pro Asp Gly Gly Ile Leu Thr Arg Phe Gly Phe Ser Ile Pro Gln
            725                 730                 735

Leu Gly Phe Thr Leu Ser Gly Ala Thr Pro Ala Asp Ala Tyr Pro Thr
            740                 745                 750

Val Asp Tyr Ala Phe Gln Tyr Asp Gly Val Asn Asp Phe Pro Lys Tyr
            755                 760                 765

Pro Leu Asn Val Phe Ala Thr Ala Asn Ala Ile Ala Gly Ile Leu Phe
770                 775                 780

Leu His Ser Gly Leu Ile Ala Leu Pro Pro Asp Leu Ala Ser Gly Val
785                 790                 795                 800

Val Gln Pro Val Ser Ser Pro Asp Val Leu Thr Thr Tyr Ile Leu Leu
                805                 810                 815

Pro Ser Gln Asp Leu Pro Leu Leu Val Pro Leu Arg Ala Ile Pro Leu
                820                 825                 830

Leu Gly Asn Pro Leu Ala Asp Leu Ile Gln Pro Asp Leu Arg Val Leu
            835                 840                 845

Val Glu Leu Gly Tyr Asp Arg Thr Ala His Gln Asp Val Pro Ser Pro
850                 855                 860

Phe Gly Leu Phe Pro Asp Val Asp Trp Ala Glu Val Ala Ala Asp Leu
865                 870                 875                 880

Gln Gln Gly Ala Val Gln Gly Val Asn Asp Ala Leu Ser Gly Leu Gly
                885                 890                 895

Leu Pro Pro Pro Trp Gln Pro Ala Leu Pro Arg Leu Phe Ser Thr
            900                 905                 910

<210> SEQ ID NO 2
<211> LENGTH: 891
<212> TYPE: PRT
<213> ORGANISM: Artificial Sequence
<220> FEATURE:
<223> OTHER INFORMATION: Synthetic Construct

<400> SEQUENCE: 2

Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
                20                  25                  30

Ser Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Ile
        50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala Gly Thr
                85                  90                  95

His Leu Ala Asn Gly Ser Met Ser Glu Val Met Met Ser Glu Ile Ala
                100                 105                 110

Gly Leu Pro Ile Pro Pro Ile Ile His Tyr Gly Ala Ile Ala Tyr Ala
            115                 120                 125

Pro Ser Gly Ala Ser Gly Lys Ala Trp His Gln Arg Thr Pro Ala Arg
        130                 135                 140
```

```
Ala Glu Gln Val Ala Leu Glu Lys Cys Gly Asp Lys Thr Cys Lys Val
145                 150                 155                 160

Val Ser Arg Phe Thr Arg Cys Gly Ala Val Ala Tyr Asn Gly Ser Lys
                165                 170                 175

Tyr Gln Gly Gly Thr Gly Leu Thr Arg Arg Ala Ala Glu Asp Asp Ala
            180                 185                 190

Val Asn Arg Leu Glu Gly Gly Arg Ile Val Asn Trp Ala Cys Asn Glu
            195                 200                 205

Leu Met Thr Ser Arg Phe Met Thr Asp Pro His Ala Met Arg Asp Met
    210                 215                 220

Ala Gly Arg Phe Glu Val His Ala Gln Thr Val Glu Asp Glu Ala Arg
225                 230                 235                 240

Arg Met Trp Ala Ser Ala Gln Asn Ile Ser Gly Ala Gly Trp Ser Gly
                245                 250                 255

Met Ala Glu Ala Thr Ser Leu Asp Thr Met Thr Gln Met Asn Gln Ala
                260                 265                 270

Phe Arg Asn Ile Val Asn Met Leu His Gly Val Arg Asp Gly Leu Val
            275                 280                 285

Arg Asp Ala Asn Asn Tyr Glu Gln Gln Glu Gln Ala Ser Gln Gln Ile
290                 295                 300

Leu Ser Ser Val Asp Ile Asn Phe Ala Val Leu Pro Pro Glu Val Asn
305                 310                 315                 320

Ser Ala Arg Ile Phe Ala Gly Ala Gly Leu Gly Pro Met Leu Ala Ala
                325                 330                 335

Ala Ser Ala Trp Asp Gly Leu Ala Glu Glu Leu His Ala Ala Ala Gly
                340                 345                 350

Ser Phe Ala Ser Val Thr Thr Gly Leu Ala Gly Asp Ala Trp His Gly
            355                 360                 365

Pro Ala Ser Leu Ala Met Thr Arg Ala Ala Ser Pro Tyr Val Gly Trp
    370                 375                 380

Leu Asn Thr Ala Ala Gly Gln Ala Ala Gln Ala Ala Gly Gln Ala Arg
385                 390                 395                 400

Leu Ala Ala Ser Ala Phe Glu Ala Thr Leu Ala Ala Thr Val Ser Pro
                405                 410                 415

Ala Met Val Ala Ala Asn Arg Thr Arg Leu Ala Ser Leu Val Ala Ala
                420                 425                 430

Asn Leu Leu Gly Gln Asn Ala Pro Ala Ile Ala Ala Ala Glu Ala Glu
            435                 440                 445

Tyr Glu Gln Ile Trp Ala Gln Asp Val Ala Ala Met Phe Gly Tyr His
    450                 455                 460

Ser Ala Ala Ser Ala Val Ala Thr Gln Leu Ala Pro Ile Gln Glu Gly
465                 470                 475                 480

Leu Gln Gln Gln Leu Gln Asn Val Leu Ala Gln Leu Ala Ser Gly Asn
                485                 490                 495

Leu Gly Ser Gly Asn Val Gly Val Gly Asn Ile Gly Asn Asp Asn Ile
            500                 505                 510

Gly Asn Ala Asn Ile Gly Phe Gly Asn Arg Gly Asp Ala Asn Ile Gly
            515                 520                 525

Ile Gly Asn Ile Gly Asp Arg Asn Leu Gly Ile Gly Asn Thr Gly Asn
            530                 535                 540

Trp Asn Ile Gly Ile Gly Ile Thr Gly Asn Gly Gln Ile Gly Phe Gly
545                 550                 555                 560

Lys Pro Ala Asn Pro Asp Val Leu Val Val Gly Asn Gly Gly Pro Gly
```

-continued

```
                565                 570                 575
    Val Thr Ala Leu Val Met Gly Gly Thr Asp Ser Leu Leu Pro Leu Pro
                580                 585                 590

Asn Ile Pro Leu Leu Glu Tyr Ala Ala Arg Phe Ile Thr Pro Val His
                595                 600                 605

Pro Gly Tyr Thr Ala Thr Phe Leu Glu Thr Pro Ser Gln Phe Phe Pro
                610                 615                 620

Phe Thr Gly Leu Asn Ser Leu Thr Tyr Asp Val Ser Val Ala Gln Gly
    625                 630                 635                 640

Val Thr Asn Leu His Thr Ala Ile Met Ala Gln Leu Ala Ala Gly Asn
                    645                 650                 655

Glu Val Val Phe Gly Thr Ser Gln Ser Ala Thr Ile Ala Thr Phe
                660                 665                 670

Glu Met Arg Tyr Leu Gln Ser Leu Pro Ala His Leu Arg Pro Gly Leu
                675                 680                 685

Asp Glu Leu Ser Phe Thr Leu Thr Gly Asn Pro Asn Arg Pro Asp Gly
                690                 695                 700

Gly Ile Leu Thr Arg Phe Gly Phe Ser Ile Pro Gln Leu Gly Phe Thr
    705                 710                 715                 720

Leu Ser Gly Ala Thr Pro Ala Asp Ala Tyr Pro Thr Val Asp Tyr Ala
                    725                 730                 735

Phe Gln Tyr Asp Gly Val Asn Asp Phe Pro Lys Tyr Pro Leu Asn Val
                740                 745                 750

Phe Ala Thr Ala Asn Ala Ile Ala Gly Ile Leu Phe Leu His Ser Gly
                755                 760                 765

Leu Ile Ala Leu Pro Pro Asp Leu Ala Ser Gly Val Val Gln Pro Val
    770                 775                 780

Ser Ser Pro Asp Val Leu Thr Thr Tyr Ile Leu Pro Ser Gln Asp
    785                 790                 795                 800

Leu Pro Leu Leu Val Pro Leu Arg Ala Ile Pro Leu Leu Gly Asn Pro
                805                 810                 815

Leu Ala Asp Leu Ile Gln Pro Asp Leu Arg Val Leu Val Glu Leu Gly
                820                 825                 830

Tyr Asp Arg Thr Ala His Gln Asp Val Pro Ser Pro Phe Gly Leu Phe
                835                 840                 845

Pro Asp Val Asp Trp Ala Glu Val Ala Ala Asp Leu Gln Gln Gly Ala
                850                 855                 860

Val Gln Gly Val Asn Asp Ala Leu Ser Gly Leu Gly Leu Pro Pro
    865                 870                 875                 880

Trp Gln Pro Ala Leu Pro Arg Leu Phe Ser Thr
                        885                 890
```

<210> SEQ ID NO 3
<211> LENGTH: 818
<212> TYPE: PRT
<213> ORGANISM: Artificial Sequence
<220> FEATURE:
<223> OTHER INFORMATION: Synthetic Construct

<400> SEQUENCE: 3

```
Met Gly Ser Ser His His His His His His Ser Ser Gly Leu Val Pro
1               5                   10                  15

Arg Gly Ser His Met Gly Thr His Leu Ala Asn Gly Ser Met Ser Glu
            20                  25                  30

Val Met Met Ser Glu Ile Ala Gly Leu Pro Ile Pro Pro Ile Ile His
```

```
            35                  40                  45
Tyr Gly Ala Ile Ala Tyr Ala Pro Ser Gly Ala Ser Gly Lys Ala Trp
 50                  55                  60
His Gln Arg Thr Pro Ala Arg Ala Glu Gln Val Ala Leu Glu Lys Cys
 65                  70                  75                  80
Gly Asp Lys Thr Cys Lys Val Val Ser Arg Phe Thr Arg Cys Gly Ala
                 85                  90                  95
Val Ala Tyr Asn Gly Ser Lys Tyr Gln Gly Gly Thr Gly Leu Thr Arg
                100                 105                 110
Arg Ala Ala Glu Asp Ala Val Asn Arg Leu Glu Gly Gly Arg Ile
            115                 120                 125
Val Asn Trp Ala Cys Asn Glu Leu Met Thr Ser Arg Phe Met Thr Asp
130                 135                 140
Pro His Ala Met Arg Asp Met Ala Gly Arg Phe Glu Val His Ala Gln
145                 150                 155                 160
Thr Val Glu Asp Glu Ala Arg Arg Met Trp Ala Ser Ala Gln Asn Ile
                165                 170                 175
Ser Gly Ala Gly Trp Ser Gly Met Ala Glu Ala Thr Ser Leu Asp Thr
                180                 185                 190
Met Thr Gln Met Asn Gln Ala Phe Arg Asn Ile Val Asn Met Leu His
            195                 200                 205
Gly Val Arg Asp Gly Leu Val Arg Asp Ala Asn Asn Tyr Glu Gln Gln
210                 215                 220
Glu Gln Ala Ser Gln Gln Ile Leu Ser Ser Val Asp Ile Asn Phe Ala
225                 230                 235                 240
Val Leu Pro Pro Glu Val Asn Ser Ala Arg Ile Phe Ala Gly Ala Gly
                245                 250                 255
Leu Gly Pro Met Leu Ala Ala Ser Ala Trp Asp Gly Leu Ala Glu
                260                 265                 270
Glu Leu His Ala Ala Ala Gly Ser Phe Ala Ser Val Thr Thr Gly Leu
            275                 280                 285
Ala Gly Asp Ala Trp His Gly Pro Ala Ser Leu Ala Met Thr Arg Ala
290                 295                 300
Ala Ser Pro Tyr Val Gly Trp Leu Asn Thr Ala Ala Gly Gln Ala Ala
305                 310                 315                 320
Gln Ala Ala Gly Gln Ala Arg Leu Ala Ala Ser Ala Phe Glu Ala Thr
                325                 330                 335
Leu Ala Ala Thr Val Ser Pro Ala Met Val Ala Ala Asn Arg Thr Arg
                340                 345                 350
Leu Ala Ser Leu Val Ala Ala Asn Leu Leu Gly Gln Asn Ala Pro Ala
            355                 360                 365
Ile Ala Ala Glu Ala Tyr Glu Gln Ile Trp Ala Gln Asp Val
370                 375                 380
Ala Ala Met Phe Gly Tyr His Ser Ala Ala Ser Ala Val Ala Thr Gln
385                 390                 395                 400
Leu Ala Pro Ile Gln Glu Gly Leu Gln Gln Leu Gln Asn Val Leu
                405                 410                 415
Ala Gln Leu Ala Ser Gly Asn Leu Gly Ser Gly Asn Val Gly Val Gly
            420                 425                 430
Asn Ile Gly Asn Asp Asn Ile Gly Asn Ala Asn Ile Gly Phe Gly Asn
            435                 440                 445
Arg Gly Asp Ala Asn Ile Gly Ile Gly Asn Ile Gly Asp Arg Asn Leu
450                 455                 460
```

Gly Ile Gly Asn Thr Gly Asn Trp Asn Ile Gly Ile Gly Ile Thr Gly
465                 470                 475                 480

Asn Gly Gln Ile Gly Phe Gly Lys Pro Ala Asn Pro Asp Val Leu Val
            485                 490                 495

Val Gly Asn Gly Gly Pro Gly Val Thr Ala Leu Val Met Gly Gly Thr
        500                 505                 510

Asp Ser Leu Leu Pro Leu Pro Asn Ile Pro Leu Leu Glu Tyr Ala Ala
            515                 520                 525

Arg Phe Ile Thr Pro Val His Pro Gly Tyr Thr Ala Thr Phe Leu Glu
            530                 535                 540

Thr Pro Ser Gln Phe Phe Pro Phe Thr Gly Leu Asn Ser Leu Thr Tyr
545                 550                 555                 560

Asp Val Ser Val Ala Gln Gly Val Thr Asn Leu His Thr Ala Ile Met
            565                 570                 575

Ala Gln Leu Ala Ala Gly Asn Glu Val Val Phe Gly Thr Ser Gln
            580                 585                 590

Ser Ala Thr Ile Ala Thr Phe Glu Met Arg Tyr Leu Gln Ser Leu Pro
            595                 600                 605

Ala His Leu Arg Pro Gly Leu Asp Glu Leu Ser Phe Thr Leu Thr Gly
            610                 615                 620

Asn Pro Asn Arg Pro Asp Gly Gly Ile Leu Thr Arg Phe Gly Phe Ser
625                 630                 635                 640

Ile Pro Gln Leu Gly Phe Thr Leu Ser Gly Ala Thr Pro Ala Asp Ala
            645                 650                 655

Tyr Pro Thr Val Asp Tyr Ala Phe Gln Tyr Asp Gly Val Asn Asp Phe
            660                 665                 670

Pro Lys Tyr Pro Leu Asn Val Phe Ala Thr Ala Asn Ala Ile Ala Gly
            675                 680                 685

Ile Leu Phe Leu His Ser Gly Leu Ile Ala Leu Pro Pro Asp Leu Ala
            690                 695                 700

Ser Gly Val Val Gln Pro Val Ser Ser Pro Asp Val Leu Thr Thr Tyr
705                 710                 715                 720

Ile Leu Leu Pro Ser Gln Asp Leu Pro Leu Val Pro Leu Arg Ala
            725                 730                 735

Ile Pro Leu Leu Gly Asn Pro Leu Ala Asp Leu Ile Gln Pro Asp Leu
            740                 745                 750

Arg Val Leu Val Glu Leu Gly Tyr Asp Arg Thr Ala His Gln Asp Val
            755                 760                 765

Pro Ser Pro Phe Gly Leu Phe Pro Asp Val Asp Trp Ala Glu Val Ala
770                 775                 780

Ala Asp Leu Gln Gln Gly Ala Val Gln Gly Val Asn Asp Ala Leu Ser
785                 790                 795                 800

Gly Leu Gly Leu Pro Pro Pro Trp Gln Pro Ala Leu Pro Arg Leu Phe
            805                 810                 815

Ser Thr

<210> SEQ ID NO 4
<211> LENGTH: 795
<212> TYPE: PRT
<213> ORGANISM: Artificial Sequence
<220> FEATURE:
<223> OTHER INFORMATION: Synthetic Construct

<400> SEQUENCE: 4

```
His Leu Ala Asn Gly Ser Met Ser Glu Val Met Met Ser Glu Ile Ala
1               5                   10                  15

Gly Leu Pro Ile Pro Pro Ile Ile His Tyr Gly Ala Ile Ala Tyr Ala
            20              25                  30

Pro Ser Gly Ala Ser Gly Lys Ala Trp His Gln Arg Thr Pro Ala Arg
            35              40                  45

Ala Glu Gln Val Ala Leu Glu Lys Cys Gly Asp Lys Thr Cys Lys Val
        50              55                  60

Val Ser Arg Phe Thr Arg Cys Gly Ala Val Ala Tyr Asn Gly Ser Lys
65                  70                  75                  80

Tyr Gln Gly Gly Thr Gly Leu Thr Arg Arg Ala Ala Glu Asp Asp Ala
                85                  90                  95

Val Asn Arg Leu Glu Gly Gly Arg Ile Val Asn Trp Ala Cys Asn Glu
        100                 105                 110

Leu Met Thr Ser Arg Phe Met Thr Asp Pro His Ala Met Arg Asp Met
            115                 120                 125

Ala Gly Arg Phe Glu Val His Ala Gln Thr Val Glu Asp Glu Ala Arg
        130                 135                 140

Arg Met Trp Ala Ser Ala Gln Asn Ile Ser Gly Ala Gly Trp Ser Gly
145                 150                 155                 160

Met Ala Glu Ala Thr Ser Leu Asp Thr Met Thr Gln Met Asn Gln Ala
                165                 170                 175

Phe Arg Asn Ile Val Asn Met Leu His Gly Val Arg Asp Gly Leu Val
            180                 185                 190

Arg Asp Ala Asn Asn Tyr Glu Gln Gln Glu Gln Ala Ser Gln Gln Ile
        195                 200                 205

Leu Ser Ser Val Asp Ile Asn Phe Ala Val Leu Pro Pro Glu Val Asn
    210                 215                 220

Ser Ala Arg Ile Phe Ala Gly Ala Gly Leu Gly Pro Met Leu Ala Ala
225                 230                 235                 240

Ala Ser Ala Trp Asp Gly Leu Ala Glu Glu Leu His Ala Ala Ala Gly
                245                 250                 255

Ser Phe Ala Ser Val Thr Thr Gly Leu Ala Gly Asp Ala Trp His Gly
            260                 265                 270

Pro Ala Ser Leu Ala Met Thr Arg Ala Ala Ser Pro Tyr Val Gly Trp
        275                 280                 285

Leu Asn Thr Ala Ala Gly Gln Ala Gln Ala Ala Gly Gln Ala Arg
    290                 295                 300

Leu Ala Ala Ser Ala Phe Glu Ala Thr Leu Ala Ala Thr Val Ser Pro
305                 310                 315                 320

Ala Met Val Ala Ala Asn Arg Thr Arg Leu Ala Ser Leu Val Ala Ala
                325                 330                 335

Asn Leu Leu Gly Gln Asn Ala Pro Ala Ile Ala Ala Glu Ala Glu
            340                 345                 350

Tyr Glu Gln Ile Trp Ala Gln Asp Val Ala Ala Met Phe Gly Tyr His
        355                 360                 365

Ser Ala Ala Ser Ala Val Ala Thr Gln Leu Ala Pro Ile Gln Glu Gly
    370                 375                 380

Leu Gln Gln Gln Leu Gln Asn Val Leu Ala Gln Leu Ala Ser Gly Asn
385                 390                 395                 400

Leu Gly Ser Gly Asn Val Gly Val Gly Asn Ile Gly Asn Asp Asn Ile
                405                 410                 415

Gly Asn Ala Asn Ile Gly Phe Gly Asn Arg Gly Asp Ala Asn Ile Gly
```

```
              420             425             430
Ile Gly Asn Ile Gly Asp Arg Asn Leu Gly Ile Gly Asn Thr Gly Asn
            435                 440                 445
Trp Asn Ile Gly Ile Gly Ile Thr Gly Asn Gly Gln Ile Gly Phe Gly
450                 455                 460
Lys Pro Ala Asn Pro Asp Val Leu Val Val Gly Asn Gly Gly Pro Gly
465                 470                 475                 480
Val Thr Ala Leu Val Met Gly Gly Thr Asp Ser Leu Leu Pro Leu Pro
                485                 490                 495
Asn Ile Pro Leu Leu Glu Tyr Ala Ala Arg Phe Ile Thr Pro Val His
            500                 505                 510
Pro Gly Tyr Thr Ala Thr Phe Leu Glu Thr Pro Ser Gln Phe Phe Pro
        515                 520                 525
Phe Thr Gly Leu Asn Ser Leu Thr Tyr Asp Val Ser Val Ala Gln Gly
        530                 535                 540
Val Thr Asn Leu His Thr Ala Ile Met Ala Gln Leu Ala Ala Gly Asn
545                 550                 555                 560
Glu Val Val Val Phe Gly Thr Ser Gln Ser Ala Thr Ile Ala Thr Phe
                565                 570                 575
Glu Met Arg Tyr Leu Gln Ser Leu Pro Ala His Leu Arg Pro Gly Leu
            580                 585                 590
Asp Glu Leu Ser Phe Thr Leu Thr Gly Asn Pro Asn Arg Pro Asp Gly
        595                 600                 605
Gly Ile Leu Thr Arg Phe Gly Phe Ser Ile Pro Gln Leu Gly Phe Thr
        610                 615                 620
Leu Ser Gly Ala Thr Pro Ala Asp Ala Tyr Pro Thr Val Asp Tyr Ala
625                 630                 635                 640
Phe Gln Tyr Asp Gly Val Asn Asp Phe Pro Lys Tyr Pro Leu Asn Val
                645                 650                 655
Phe Ala Thr Ala Asn Ala Ile Ala Gly Ile Leu Phe Leu His Ser Gly
            660                 665                 670
Leu Ile Ala Leu Pro Pro Asp Leu Ala Ser Gly Val Val Gln Pro Val
        675                 680                 685
Ser Ser Pro Asp Val Leu Thr Thr Tyr Ile Leu Leu Pro Ser Gln Asp
        690                 695                 700
Leu Pro Leu Leu Val Pro Leu Arg Ala Ile Pro Leu Leu Gly Asn Pro
705                 710                 715                 720
Leu Ala Asp Leu Ile Gln Pro Asp Leu Arg Val Leu Val Glu Leu Gly
                725                 730                 735
Tyr Asp Arg Thr Ala His Gln Asp Val Pro Ser Pro Phe Gly Leu Phe
            740                 745                 750
Pro Asp Val Asp Trp Ala Glu Val Ala Ala Asp Leu Gln Gln Gly Ala
        755                 760                 765
Val Gln Gly Val Asn Asp Ala Leu Ser Gly Leu Gly Leu Pro Pro Pro
        770                 775                 780
Trp Gln Pro Ala Leu Pro Arg Leu Phe Ser Thr
785                 790                 795
```

<210> SEQ ID NO 5
<211> LENGTH: 143
<212> TYPE: PRT
<213> ORGANISM: Mycobacterium tuberculosis

<400> SEQUENCE: 5

```
Met Ile Thr Asn Leu Arg Arg Arg Thr Ala Met Ala Ala Ala Gly Leu
1               5                   10                  15

Gly Ala Ala Leu Gly Leu Gly Ile Leu Leu Val Pro Thr Val Asp Ala
            20                  25                  30

His Leu Ala Asn Gly Ser Met Ser Glu Val Met Met Ser Glu Ile Ala
        35                  40                  45

Gly Leu Pro Ile Pro Pro Ile Ile His Tyr Gly Ala Ile Ala Tyr Ala
    50                  55                  60

Pro Ser Gly Ala Ser Gly Lys Ala Trp His Gln Arg Thr Pro Ala Arg
65                  70                  75                  80

Ala Glu Gln Val Ala Leu Glu Lys Cys Gly Asp Lys Thr Cys Lys Val
                85                  90                  95

Val Ser Arg Phe Thr Arg Cys Gly Ala Val Ala Tyr Asn Gly Ser Lys
            100                 105                 110

Tyr Gln Gly Gly Thr Gly Leu Thr Arg Arg Ala Ala Glu Asp Asp Ala
        115                 120                 125

Val Asn Arg Leu Glu Gly Gly Arg Ile Val Asn Trp Ala Cys Asn
    130                 135                 140

<210> SEQ ID NO 6
<211> LENGTH: 98
<212> TYPE: PRT
<213> ORGANISM: Mycobacterium tuberculosis

<400> SEQUENCE: 6

Met Thr Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser

<210> SEQ ID NO 7
<211> LENGTH: 580
<212> TYPE: PRT
<213> ORGANISM: Mycobacterium tuberculosis

<400> SEQUENCE: 7

Met Asn Phe Ala Val Leu Pro Pro Glu Val Asn Ser Ala Arg Ile Phe
1               5                   10                  15

Ala Gly Ala Gly Leu Gly Pro Met Leu Ala Ala Ala Ser Ala Trp Asp
            20                  25                  30

Gly Leu Ala Glu Glu Leu His Ala Ala Ala Gly Ser Phe Ala Ser Val
        35                  40                  45

Thr Thr Gly Leu Ala Gly Asp Ala Trp His Gly Pro Ala Ser Leu Ala
    50                  55                  60

Met Thr Arg Ala Ala Ser Pro Tyr Val Gly Trp Leu Asn Thr Ala Ala
65                  70                  75                  80

Gly Gln Ala Ala Gln Ala Ala Gly Gln Ala Arg Leu Ala Ala Ser Ala
```

```
                    85                  90                  95
Phe Glu Ala Thr Leu Ala Ala Thr Val Ser Pro Ala Met Val Ala Ala
                100                 105                 110
Asn Arg Thr Arg Leu Ala Ser Leu Val Ala Ala Asn Leu Leu Gly Gln
            115                 120                 125
Asn Ala Pro Ala Ile Ala Ala Glu Ala Glu Tyr Glu Gln Ile Trp
        130                 135                 140
Ala Gln Asp Val Ala Ala Met Phe Gly Tyr His Ser Ala Ala Ser Ala
145                 150                 155                 160
Val Ala Thr Gln Leu Ala Pro Ile Gln Glu Gly Leu Gln Gln Gln Leu
                165                 170                 175
Gln Asn Val Leu Ala Gln Leu Ala Ser Gly Asn Leu Gly Ser Gly Asn
            180                 185                 190
Val Gly Val Gly Asn Ile Gly Asn Asp Asn Ile Gly Asn Ala Asn Ile
        195                 200                 205
Gly Phe Gly Asn Arg Gly Asp Ala Asn Ile Gly Ile Gly Asn Ile Gly
    210                 215                 220
Asp Arg Asn Leu Gly Ile Gly Asn Thr Gly Asn Trp Asn Ile Gly Ile
225                 230                 235                 240
Gly Ile Thr Gly Asn Gly Gln Ile Gly Phe Gly Lys Pro Ala Asn Pro
                245                 250                 255
Asp Val Leu Val Val Gly Asn Gly Gly Pro Gly Val Thr Ala Leu Val
            260                 265                 270
Met Gly Gly Thr Asp Ser Leu Leu Pro Leu Pro Asn Ile Pro Leu Leu
        275                 280                 285
Glu Tyr Ala Ala Arg Phe Ile Thr Pro Val His Pro Gly Tyr Thr Ala
    290                 295                 300
Thr Phe Leu Glu Thr Pro Ser Gln Phe Pro Phe Thr Gly Leu Asn
305                 310                 315                 320
Ser Leu Thr Tyr Asp Val Ser Val Ala Gln Gly Val Thr Asn Leu His
                325                 330                 335
Thr Ala Ile Met Ala Gln Leu Ala Ala Gly Asn Glu Val Val Val Phe
            340                 345                 350
Gly Thr Ser Gln Ser Ala Thr Ile Ala Thr Phe Glu Met Arg Tyr Leu
        355                 360                 365
Gln Ser Leu Pro Ala His Leu Arg Pro Gly Leu Asp Glu Leu Ser Phe
    370                 375                 380
Thr Leu Thr Gly Asn Pro Asn Arg Pro Asp Gly Gly Ile Leu Thr Arg
385                 390                 395                 400
Phe Gly Phe Ser Ile Pro Gln Leu Gly Phe Thr Leu Ser Gly Ala Thr
                405                 410                 415
Pro Ala Asp Ala Tyr Pro Thr Val Asp Tyr Ala Phe Gln Tyr Asp Gly
            420                 425                 430
Val Asn Asp Phe Pro Lys Tyr Pro Leu Asn Val Phe Ala Thr Ala Asn
        435                 440                 445
Ala Ile Ala Gly Ile Leu Phe Leu His Ser Gly Leu Ile Ala Leu Pro
    450                 455                 460
Pro Asp Leu Ala Ser Gly Val Val Gln Pro Val Ser Ser Pro Asp Val
465                 470                 475                 480
Leu Thr Thr Tyr Ile Leu Leu Pro Ser Gln Asp Leu Pro Leu Leu Val
                485                 490                 495
Pro Leu Arg Ala Ile Pro Leu Leu Gly Asn Pro Leu Ala Asp Leu Ile
            500                 505                 510
```

```
Gln Pro Asp Leu Arg Val Leu Val Glu Leu Gly Tyr Asp Arg Thr Ala
            515                 520                 525

His Gln Asp Val Pro Ser Pro Phe Gly Leu Phe Pro Asp Val Asp Trp
            530                 535                 540

Ala Glu Val Ala Ala Asp Leu Gln Gln Gly Ala Val Gln Gly Val Asn
545                 550                 555                 560

Asp Ala Leu Ser Gly Leu Gly Leu Pro Pro Pro Trp Gln Pro Ala Leu
            565                 570                 575

Pro Arg Leu Phe
            580

<210> SEQ ID NO 8
<211> LENGTH: 94
<212> TYPE: PRT
<213> ORGANISM: Mycobacterium tuberculosis

<400> SEQUENCE: 8

Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
            20                  25                  30

Ser Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Ile
        50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
            85                  90
```